(12) United States Patent
Nassif

(10) Patent No.: US 11,642,537 B2
(45) Date of Patent: May 9, 2023

(54) CHARGING DEVICE WITH OFF-CENTER COIL

(71) Applicant: Axonics, Inc., Irvine, CA (US)

(72) Inventor: Rabih Nassif, Santa Ana, CA (US)

(73) Assignee: Axonics, Inc., Irvine, CA (US)

( * ) Notice: Subject to any disclaimer, the term of this patent is extended or adjusted under 35 U.S.C. 154(b) by 91 days.

(21) Appl. No.: 16/816,006

(22) Filed: Mar. 11, 2020

(65) Prior Publication Data

US 2020/0289832 A1 Sep. 17, 2020

Related U.S. Application Data

(60) Provisional application No. 62/816,829, filed on Mar. 11, 2019.

(51) Int. Cl.
*A61N 1/378* (2006.01)
*A61N 1/05* (2006.01)
*A61N 1/36* (2006.01)
*A61N 1/372* (2006.01)
*A61N 1/02* (2006.01)

(52) U.S. Cl.
CPC ........... *A61N 1/3787* (2013.01); *A61N 1/025* (2013.01); *A61N 1/0551* (2013.01); *A61N 1/36125* (2013.01); *A61N 1/37223* (2013.01)

(58) Field of Classification Search
None
See application file for complete search history.

(56) References Cited

U.S. PATENT DOCUMENTS

| 3,057,356 A | 10/1962 | Greatbatch |
| 3,348,548 A | 10/1967 | Chardack |
| 3,646,940 A | 3/1972 | Timm et al. |
| 3,824,129 A | 7/1974 | Fagan, Jr. |
| 3,825,015 A | 7/1974 | Berkovits |

(Continued)

FOREIGN PATENT DOCUMENTS

| AT | 520440 | 9/2011 |
| AU | 4664800 | 11/2000 |

(Continued)

OTHER PUBLICATIONS

US 9,601,939 B2, 03/2017, Cong et al. (withdrawn)

(Continued)

*Primary Examiner* — Erin M Piateski
(74) *Attorney, Agent, or Firm* — Gordon Rees Scully; Mansukhani, LLP

(57) ABSTRACT

Systems and methods for improved power transmission are disclosed herein. The system can include an implantable neurostimulator for delivering the one or more electrical pulses to a patient's body. The implantable neurostimulator can include a hermetic housing made of a biocompatible material, an energy storage feature for powering the implantable neurostimulator, a receiving coil assembly including an elongate wire winding wound around a first ferritic core, and control circuitry for controlling recharging of the energy storage feature. The system can include a charging device for wirelessly delivering energy to the implantable neurostimulator. The charging device can include a sending coil assembly including a planar wire winding coupled to a surface of a second ferritic core.

24 Claims, 13 Drawing Sheets

(56) References Cited

U.S. PATENT DOCUMENTS

| | | |
|---|---|---|
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,141,365 A | 2/1979 | Fischell et al. |
| 4,166,469 A | 9/1979 | Littleford |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,468,723 A | 8/1984 | Hughes |
| 4,512,351 A | 4/1985 | Pohndorf |
| 4,550,731 A | 11/1985 | Batina et al. |
| 4,553,702 A | 11/1985 | Coffee et al. |
| 4,558,702 A | 12/1985 | Barreras et al. |
| 4,654,880 A | 3/1987 | Sontag |
| 4,662,382 A | 5/1987 | Sluetz et al. |
| 4,673,867 A | 6/1987 | Davis |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,143,089 A | 9/1992 | Alt |
| 5,193,539 A | 3/1993 | Schulman et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | deCoriolis et al. |
| 5,439,485 A | 8/1995 | Mar et al. |
| 5,450,088 A | 9/1995 | Meier et al. |
| 5,476,499 A | 12/1995 | Hirschberg |
| 5,484,445 A | 1/1996 | Knuth |
| 5,558,097 A | 9/1996 | Jacobson et al. |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,755,748 A | 5/1998 | Borza |
| 5,871,532 A | 2/1999 | Schroeppel |
| 5,876,423 A | 3/1999 | Braun |
| 5,877,472 A | 3/1999 | Campbell et al. |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,061,596 A | 5/2000 | Richmond et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,164,284 A | 12/2000 | Schulman et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,208,902 B1 | 3/2001 | Boveja |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,313,779 B1 | 11/2001 | Leung et al. |
| 6,315,721 B2 | 11/2001 | Schulman et al. |
| 6,316,909 B1 | 11/2001 | Honda et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,331,744 B1 | 12/2001 | Chen et al. |
| 6,341,073 B1 | 1/2002 | Lee |
| 6,354,991 B1 | 3/2002 | Gross et al. |
| 6,360,750 B1 | 3/2002 | Gerber et al. |
| 6,381,496 B1 | 4/2002 | Meadows et al. |
| 6,389,318 B1 | 5/2002 | Zarinetchi et al. |
| 6,393,325 B1 | 5/2002 | Mann et al. |
| 6,415,186 B1 | 7/2002 | Chim et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,447,448 B1 | 9/2002 | Ishikawa et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion et al. |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,521,350 B2 | 2/2003 | Fey et al. |
| 6,542,846 B1 | 4/2003 | Miller et al. |
| 6,553,263 B1 | 4/2003 | Meadows et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |
| 6,664,763 B2 | 12/2003 | Echarri et al. |
| 6,685,638 B1 | 2/2004 | Taylor et al. |
| 6,701,188 B2 | 3/2004 | Stroebel et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |

(56) References Cited

U.S. PATENT DOCUMENTS

| | | |
|---|---|---|
| 6,864,755 B2 | 3/2005 | Moore |
| 6,885,894 B2 | 4/2005 | Stessman |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,286,881 B2 | 10/2007 | Schommer et al. |
| 7,289,761 B2 | 10/2007 | Mazar et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,525,293 B1 | 4/2009 | Notohamiprodjo et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,599,743 B2 | 10/2009 | Hassler, Jr. et al. |
| 7,617,002 B2 | 11/2009 | Goetz |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,880,337 B2 | 2/2011 | Farkas |
| 7,904,167 B2 | 3/2011 | Klosterman et al. |
| 7,912,547 B2 | 3/2011 | Tseng et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,217,535 B2 | 7/2012 | Uchida et al. |
| 8,219,196 B2 | 7/2012 | Torgerson |
| 8,219,202 B2 | 7/2012 | Giftakis et al. |
| 8,219,205 B2 | 7/2012 | Tseng et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,310,108 B2 | 11/2012 | Inoue et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |

(56) References Cited

U.S. PATENT DOCUMENTS

| | | |
|---|---|---|
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,612,002 B2 | 12/2013 | Faltys et al. |
| 8,620,436 B2 | 12/2013 | Parramon et al. |
| 8,620,454 B2 | 12/2013 | Wahlstrand et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,655,453 B2 | 2/2014 | Werder et al. |
| 8,700,175 B2 | 4/2014 | Fell |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,774,924 B2 | 7/2014 | Weiner |
| 8,774,942 B2 | 7/2014 | Lund et al. |
| 8,805,524 B2 | 8/2014 | Woods et al. |
| 8,855,767 B2 | 10/2014 | Faltys et al. |
| 8,918,174 B2 | 12/2014 | Woods et al. |
| 8,954,148 B2 | 2/2015 | Labbe et al. |
| 8,989,861 B2 | 3/2015 | Su et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,099,884 B2 | 8/2015 | Jung et al. |
| 9,106,094 B2 | 8/2015 | Negishi et al. |
| 9,108,063 B2 | 8/2015 | Olson et al. |
| 9,132,276 B2 | 9/2015 | Meskens |
| 9,144,680 B2 | 9/2015 | Kaula et al. |
| 9,149,635 B2 | 10/2015 | Denison et al. |
| 9,155,885 B2 | 10/2015 | Wei et al. |
| 9,155,901 B2 | 10/2015 | Dearden et al. |
| 9,166,321 B2 | 10/2015 | Smith et al. |
| 9,166,441 B2 | 10/2015 | Dearden et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,205,273 B2 | 12/2015 | Dearden et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber |
| 9,283,394 B2 | 3/2016 | Whitehurst et al. |
| 9,295,851 B2 | 3/2016 | Gordon et al. |
| 9,306,399 B2 | 4/2016 | Kim et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,319,777 B2 | 4/2016 | Aoki et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,391,461 B2 | 7/2016 | Kim et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,597,521 B2 | 3/2017 | Plotkin et al. |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,685,824 B2 | 6/2017 | Iijima et al. |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,780,596 B2 | 10/2017 | Dearden et al. |
| 9,782,596 B2 | 10/2017 | Vamos et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,436 B2 | 1/2018 | Dearden et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |

(56) References Cited

U.S. PATENT DOCUMENTS

| | | |
|---|---|---|
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | LeBaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,447,083 B2 | 10/2019 | Dearden et al. |
| 10,448,889 B2 | 10/2019 | Gerber et al. |
| 10,449,377 B2 | 10/2019 | Dearden et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 10,603,500 B2 | 3/2020 | Nassif et al. |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0062141 A1 | 5/2002 | Moore |
| 2002/0116042 A1 | 8/2002 | Boling |
| 2002/0140399 A1 | 10/2002 | Echarri et al. |
| 2002/0156513 A1 | 10/2002 | Borkan |
| 2002/0177884 A1 | 11/2002 | Ahn et al. |
| 2003/0028072 A1 | 2/2003 | Fischell et al. |
| 2003/0040291 A1 | 2/2003 | Brewer |
| 2003/0078633 A1 | 4/2003 | Firlik et al. |
| 2003/0114899 A1 | 6/2003 | Woods et al. |
| 2003/0212440 A1 | 11/2003 | Boveja |
| 2004/0098068 A1 | 5/2004 | Carbunaru et al. |
| 2004/0106963 A1 | 6/2004 | Tsukamoto et al. |
| 2004/0210290 A1 | 10/2004 | Omar-Pasha |
| 2004/0250820 A1 | 12/2004 | Forsell |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0068019 A1 | 3/2005 | Nakamura et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1* | 4/2005 | Schommer .......... A61N 1/3787 607/61 |
| 2005/0104577 A1 | 5/2005 | Matei et al. |
| 2005/0140482 A1 | 6/2005 | Cheng et al. |
| 2005/0187590 A1 | 8/2005 | Boveja et al. |
| 2005/0288743 A1* | 12/2005 | Ahn .................... A61N 1/3787 607/61 |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0149345 A1 | 7/2006 | Boggs, II et al. |
| 2006/0200205 A1 | 9/2006 | Haller |
| 2006/0206166 A1 | 9/2006 | Weiner |
| 2006/0247737 A1 | 11/2006 | Olson et al. |
| 2006/0253173 A1 | 11/2006 | Tseng et al. |
| 2007/0032836 A1 | 2/2007 | Thrope et al. |
| 2007/0060968 A1 | 3/2007 | Strother et al. |
| 2007/0060980 A1 | 3/2007 | Strother et al. |
| 2007/0073357 A1 | 3/2007 | Rooney et al. |
| 2007/0185546 A1 | 8/2007 | Tseng et al. |
| 2007/0239224 A1 | 10/2007 | Bennett et al. |
| 2007/0265675 A1 | 11/2007 | Lund et al. |
| 2007/0293914 A1 | 12/2007 | Woods et al. |
| 2008/0011800 A1 | 1/2008 | Vandevere |
| 2008/0065182 A1 | 3/2008 | Strother et al. |
| 2008/0081962 A1 | 4/2008 | Miller et al. |
| 2008/0082135 A1 | 4/2008 | Arcot-Krishnamurthy et al. |
| 2008/0132961 A1 | 6/2008 | Jaax et al. |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0172109 A1 | 7/2008 | Rahman et al. |
| 2008/0183236 A1 | 7/2008 | Gerber |
| 2008/0278974 A1 | 11/2008 | Wu |
| 2008/0300654 A1 | 12/2008 | Lambert et al. |
| 2008/0303480 A1 | 12/2008 | Prutchi et al. |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0146608 A1 | 6/2009 | Lee |
| 2009/0227829 A1 | 9/2009 | Burnett et al. |
| 2009/0259273 A1 | 10/2009 | Figueiredo et al. |
| 2009/0284220 A1 | 11/2009 | Toncich et al. |
| 2010/0076254 A1 | 3/2010 | Jimenez et al. |
| 2010/0076516 A1 | 3/2010 | Padiy et al. |
| 2010/0076534 A1 | 3/2010 | Mock |

(56) References Cited

U.S. PATENT DOCUMENTS

| | | |
|---|---|---|
| 2010/0100158 A1 | 4/2010 | Thrope et al. |
| 2010/0256710 A1 | 10/2010 | Dinsmoor et al. |
| 2010/0259110 A1 | 10/2010 | Kurs et al. |
| 2010/0274319 A1 | 10/2010 | Meskens |
| 2010/0331918 A1 | 12/2010 | Digiore et al. |
| 2011/0004269 A1 | 1/2011 | Strother et al. |
| 2011/0004278 A1 | 1/2011 | Aghassian et al. |
| 2011/0009924 A1 | 1/2011 | Meskens |
| 2011/0022125 A1 | 1/2011 | Olson et al. |
| 2011/0084656 A1 | 4/2011 | Gao |
| 2011/0093045 A1 | 4/2011 | Moffitt |
| 2011/0101790 A1 | 5/2011 | Budgett |
| 2011/0121777 A1 | 5/2011 | Carbunaru et al. |
| 2011/0152959 A1 | 6/2011 | Sherwood et al. |
| 2011/0160799 A1 | 6/2011 | Mishra et al. |
| 2011/0169446 A1 | 7/2011 | Kondo |
| 2011/0193688 A1 | 8/2011 | Forsell |
| 2011/0234155 A1 | 9/2011 | Chen et al. |
| 2011/0257701 A1 | 10/2011 | Strother et al. |
| 2011/0270269 A1 | 11/2011 | Swoyer et al. |
| 2011/0278948 A1 | 11/2011 | Forsell |
| 2011/0282416 A1 | 11/2011 | Hamann et al. |
| 2011/0288615 A1 | 11/2011 | Armstrong et al. |
| 2011/0301667 A1 | 12/2011 | Olson et al. |
| 2011/0313427 A1 | 12/2011 | Gindele et al. |
| 2012/0012630 A1 | 1/2012 | Lui et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0119699 A1 | 5/2012 | Carbunaru et al. |
| 2012/0123505 A1 | 5/2012 | Kothandaraman |
| 2012/0130448 A1 | 5/2012 | Woods et al. |
| 2012/0139485 A1 | 6/2012 | Olson et al. |
| 2012/0150259 A1 | 6/2012 | Meskens |
| 2012/0161540 A1 | 6/2012 | Moon et al. |
| 2012/0212178 A1 | 8/2012 | Kim |
| 2012/0214418 A1 | 8/2012 | Lee et al. |
| 2012/0235634 A1 | 9/2012 | Hall et al. |
| 2012/0242276 A1 | 9/2012 | Jung et al. |
| 2012/0245649 A1 | 9/2012 | Bohori et al. |
| 2012/0259381 A1 | 10/2012 | Smith et al. |
| 2012/0262108 A1 | 10/2012 | Olson et al. |
| 2012/0267960 A1 | 10/2012 | Low et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2012/0283800 A1 | 11/2012 | Perryman et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0020988 A1 | 1/2013 | Kim et al. |
| 2013/0023958 A1 | 1/2013 | Fell |
| 2013/0026982 A1 | 1/2013 | Rothenbaum |
| 2013/0033117 A1 | 2/2013 | Kim et al. |
| 2013/0051083 A1 | 2/2013 | Zhao |
| 2013/0058380 A1 | 3/2013 | Kim et al. |
| 2013/0063084 A1 | 3/2013 | Tilvis et al. |
| 2013/0096651 A1 | 4/2013 | Ozawa et al. |
| 2013/0096653 A1 | 4/2013 | Winstrom |
| 2013/0119774 A1 | 5/2013 | Ichikawa |
| 2013/0127404 A1 | 5/2013 | Maenpaa |
| 2013/0148768 A1 | 6/2013 | Kim |
| 2013/0150925 A1 | 6/2013 | Vamos et al. |
| 2013/0184785 A1 | 7/2013 | Aghassian |
| 2013/0187478 A1 | 7/2013 | Bae et al. |
| 2013/0197607 A1 | 8/2013 | Wilder et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0218228 A1 | 8/2013 | Goossen |
| 2013/0241304 A1 | 9/2013 | Bae |
| 2013/0241306 A1 | 9/2013 | Aber et al. |
| 2013/0303942 A1 | 11/2013 | Damaser et al. |
| 2013/0310630 A1 | 11/2013 | Smith et al. |
| 2013/0310894 A1 | 11/2013 | Trier |
| 2013/0331909 A1 | 12/2013 | Gerber |
| 2013/0331910 A1 | 12/2013 | Lamont et al. |
| 2014/0002013 A1 | 1/2014 | Kossi et al. |
| 2014/0021914 A1 | 1/2014 | Martin et al. |
| 2014/0028267 A1 | 1/2014 | Lee |
| 2014/0031892 A1* | 1/2014 | Mashiach ............ A61N 1/0526 607/44 |
| 2014/0031903 A1 | 1/2014 | Mashiach et al. |
| 2014/0074185 A1 | 3/2014 | Fell et al. |
| 2014/0107743 A1 | 4/2014 | Wahlstrand et al. |
| 2014/0207220 A1 | 7/2014 | Boling et al. |
| 2014/0222112 A1 | 8/2014 | Fell |
| 2014/0237806 A1 | 8/2014 | Smith et al. |
| 2014/0266025 A1 | 9/2014 | Jakubowski |
| 2014/0277268 A1 | 9/2014 | Lee |
| 2014/0277270 A1 | 9/2014 | Parramon et al. |
| 2015/0028798 A1 | 1/2015 | Dearden et al. |
| 2015/0028805 A1 | 1/2015 | Dearden et al. |
| 2015/0028806 A1 | 1/2015 | Dearden et al. |
| 2015/0088227 A1 | 3/2015 | Shishilla et al. |
| 2015/0094790 A1 | 4/2015 | Shishilla et al. |
| 2015/0100106 A1 | 4/2015 | Shishilla et al. |
| 2015/0123608 A1 | 5/2015 | Dearden et al. |
| 2015/0127069 A1 | 5/2015 | Dearden et al. |
| 2015/0134027 A1 | 5/2015 | Kaula et al. |
| 2015/0142081 A1 | 5/2015 | Dearden et al. |
| 2015/0214604 A1 | 7/2015 | Zhao et al. |
| 2015/0335888 A1 | 11/2015 | Demers et al. |
| 2015/0335893 A1 | 11/2015 | Parker |
| 2016/0022996 A1 | 1/2016 | Kaula et al. |
| 2016/0114177 A1 | 4/2016 | Colvin et al. |
| 2016/0126771 A1 | 5/2016 | Aghassian et al. |
| 2016/0199657 A1* | 7/2016 | Jiang ............... A61N 1/3787 607/61 |
| 2016/0199658 A1 | 7/2016 | Nassif et al. |
| 2017/0095667 A1 | 4/2017 | Yakovlev et al. |
| 2017/0127196 A1 | 5/2017 | Blum et al. |
| 2017/0189698 A1 | 7/2017 | Dellamano et al. |
| 2017/0197079 A1 | 7/2017 | Illegems et al. |
| 2017/0216609 A1 | 8/2017 | Nassif et al. |
| 2017/0340878 A1 | 11/2017 | Wahlstrand et al. |
| 2017/0353047 A1 | 12/2017 | Dearden et al. |
| 2018/0021587 A1 | 1/2018 | Strother et al. |
| 2018/0036477 A1 | 2/2018 | Olson et al. |
| 2018/0133489 A1 | 5/2018 | Dearden et al. |
| 2019/0269918 A1 | 9/2019 | Parker |
| 2019/0351244 A1 | 11/2019 | Shishilla et al. |
| 2019/0358395 A1 | 11/2019 | Olson et al. |
| 2020/0106302 A1 | 4/2020 | Dearden et al. |

FOREIGN PATENT DOCUMENTS

| | | |
|---|---|---|
| AU | 5123800 | 11/2000 |
| AU | 2014296323 | 7/2019 |
| CA | 2371378 | 11/2000 |
| CA | 2554676 | 9/2005 |
| CA | 2919462 | 3/2018 |
| CN | 101583307 | 11/2009 |
| CN | 101827630 | 9/2010 |
| CN | 101980412 | 2/2011 |
| CN | 101385890 | 3/2011 |
| CN | 102724017 | 10/2012 |
| CN | 105263571 | 1/2016 |
| CN | 105263572 | 1/2016 |
| CN | 105263571 | 6/2017 |
| DE | 3146182 | 6/1983 |
| DE | 102010006837 | 8/2011 |
| EP | 0656218 | 6/1995 |
| EP | 1205004 | 5/2002 |
| EP | 1680182 | 7/2006 |
| EP | 1904153 | 4/2008 |
| EP | 2243509 | 10/2010 |
| EP | 2498873 | 9/2012 |
| EP | 2731673 | 5/2014 |
| EP | 3027270 | 6/2016 |
| EP | 3027271 | 6/2016 |
| EP | 3028365 | 6/2016 |

(56) References Cited

FOREIGN PATENT DOCUMENTS

| | | |
|---|---|---|
| ES | 2395128 | 2/2013 |
| HK | 1098715 | 3/2012 |
| JP | 2000197275 | 7/2000 |
| JP | 3212134 | 9/2001 |
| JP | 2002198743 | 7/2002 |
| JP | 2003047179 | 2/2003 |
| JP | 2004103465 | 4/2004 |
| JP | 2005525705 | 8/2005 |
| JP | 2007268293 | 10/2007 |
| JP | 4125357 | 7/2008 |
| JP | 2012210117 | 10/2012 |
| JP | 2013121258 | 6/2013 |
| JP | 2013530668 | 7/2013 |
| JP | 2016528974 | 9/2016 |
| JP | 2016533152 | 10/2016 |
| JP | 6503351 | 3/2019 |
| WO | 96040367 | 5/1996 |
| WO | 9640367 | 12/1996 |
| WO | 9809588 | 3/1998 |
| WO | 9820933 | 5/1998 |
| WO | 9906108 | 2/1999 |
| WO | 9918879 | 4/1999 |
| WO | 9934870 | 7/1999 |
| WO | 9942173 | 8/1999 |
| WO | 2000056677 | 9/2000 |
| WO | 0065682 | 11/2000 |
| WO | 0066221 | 11/2000 |
| WO | 0069012 | 11/2000 |
| WO | 01037926 | 5/2001 |
| WO | 0183029 | 11/2001 |
| WO | 2002003408 | 1/2002 |
| WO | 0209808 | 2/2002 |
| WO | 02094139 | 11/2002 |
| WO | 03022359 | 3/2003 |
| WO | 2004021876 | 3/2004 |
| WO | 2004022130 | 5/2004 |
| WO | 2004103465 | 12/2004 |
| WO | 2005037364 | 4/2005 |
| WO | 2005037365 | 4/2005 |
| WO | 2005037370 | 4/2005 |
| WO | 2005039698 | 5/2005 |
| WO | 2005079295 | 9/2005 |
| WO | 2005081740 | 9/2005 |
| WO | 2007015599 | 2/2007 |
| WO | 2007081714 | 7/2007 |
| WO | 2007136657 | 11/2007 |
| WO | 2008021524 | 2/2008 |
| WO | 2008038202 | 4/2008 |
| WO | 2008151059 | 12/2008 |
| WO | 2009051539 | 4/2009 |
| WO | 2009055856 | 5/2009 |
| WO | 2009091267 | 7/2009 |
| WO | 2009134471 | 11/2009 |
| WO | 2010042055 | 4/2010 |
| WO | 2010042056 | 4/2010 |
| WO | 2010042057 | 4/2010 |
| WO | 2010059096 | 5/2010 |
| WO | 2011059565 | 5/2011 |
| WO | 2011090736 | 7/2011 |
| WO | 2011119352 | 9/2011 |
| WO | 2012044103 | 4/2012 |
| WO | 2012067971 | 5/2012 |
| WO | 2012103519 | 8/2012 |
| WO | 2012129061 | 9/2012 |
| WO | 2013018787 | 2/2013 |
| WO | 2013038617 | 3/2013 |
| WO | 2013072553 | 5/2013 |
| WO | 2013109605 | 7/2013 |
| WO | 2013141884 | 9/2013 |
| WO | 2015017474 | 2/2015 |
| WO | 2015017475 | 2/2015 |
| WO | 2015017475 | 4/2015 |

OTHER PUBLICATIONS

Bu-802a: How Does Rising Internal Resistance Affect Performance? Understanding the Importance of Low Conductivity, Battery University, Available Online at: https://batteryuniversity.com/learn/article/rising_internal_resistance, Accessed from Internet on May 15, 2020, 10 pages.
DOE Handbook: Primer on Lead-Acid Storage Batteries, United States Department of Energy, Available Online at: htt12s://www.stan dards.doe.gov/standards- documents/ I 000/1084-bhdbk-1995/@@images/file, Sep. 1995, 54 pages.
Medical Electrical Equipment—Part 1: General Requirements for Safety, British Standard, BS EN 60601-1:1990-BS5724-1:1989, Mar. 1979, 200 pages.
Summary of Safety and Effectiveness, Medtronic InterStim System for Urinary Control, Apr. 15, 1999, pp. 1-18.
The Advanced Bionics PRECISION™ Spinal Cord Stimulator System, Advanced Bionics Corporation, Apr. 27, 2004, pp. 1-18.
UL Standard for Safety for Medical and Dental Equipment, Underwriters Laboratories 544, 4th edition, Dec. 30, 1998, 128 pages.
Barnhart et al., "A Fixed-Rate Rechargeable Cardiac Pacemaker", Applied Physics Laboratory Technical Digest, Jan.-Feb. 1970, pp. 2-9.
Benditt et al., "A Combined Atrial/Ventricular Lead for Permanent Dual-Chamber Cardiac Pacing Applications", Chest, vol. 83, No. 6, Jun. 1983, pp. 929-931.
Boiocchi et al., "Self-Calibration in High Speed Current Steering CMOS D/A Converters", Advanced A-D and D-A Conversion Techniques and their Applications, Second International Conference on Cambridge, Jul. 1994, pp. 148-152.
Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.
Boyce et al., "Research Related to the Development of an Artificial Electrical Stimulator for the Paralyzed Human Bladder: A Review", The Journal of Urology, vol. 91, No. 1, Jan. 1964, pp. 41-51.
Bradley et al., "Further Experience with the Radio Transmitter Receiver Unit for the Neurogenic Bladder", Journal of Neurosurgery, vol. 20, No. 11, Nov. 1963, pp. 953-960.
Broggi et al., "Electrical Stimulation of the Gasserian Ganglion for Facial Pain: Preliminary Results", Acta Neurochirurgica, vol. 39, 1987, pp. 144-146.
Cameron et al., "Effects of Posture on Stimulation Parameters in Spinal Cord Stimulation", Neuromodulation, vol. 1, No. 4, Oct. 1998, pp. 177-183.
Connelly et al., "Atrial Pacing Leads Following Open Heart Surgery: Active or Passive Fixation?", Pacing and Clinical Electrophysiology, vol. 20, No. 10, Oct. 1997, pp. 2429-2433.
Fischell , "The Development of Implantable Medical Devices at the Applied Physics Laboratory", Johns Hopkins Applied Physics Laboratory Technical Digest, vol. 13 No. 1, 1992, pp. 233-243.
Gaunt et al., "Control of Urinary Bladder Function with Devices: Successes and Failures", Progress in Brain Research, vol. 152, 2006, pp. 1-24.
Ghovanloo et al., "A Small Size Large Voltage Compliance Programmable Current Source for Biomedical Implantable Microstimulators", Proceedings of the 25th Annual International Conference of the Institute of Electrical and Electronics Engineers, Engineering in Medicine and Biology Society, Sep. 17-21, 2003, pp. 1979-1982.
Gudnason , "A Low-Power ASK Demodulator for Inductively Coupled Implantable Electronics", Solid-State Circuits Conference, 2000, Esscirc ''00, Proceedings of the 26rd European, Institute of Electrical and Electronics Engineers, Sep. 19, 2000, pp. 385-388.
Helland , "Technical Improvements to be Achieved by the Year 2000: Leads and Connector Technology", Rate Adaptive Cardiac Pacing, Springer Verlag, 1993, pp. 279-292.
Hidefjall , "The Pace of Innovation—Patterns of Innovation in the Cardiac Pacemaker Industry", Linkoping University Press, 1997, 398 pages.
Humaynu et al., "A Variable Range Bi-Phasic Current Stimulus Driver Circuitry for an Implantable Retinal Prosthetic Device",

(56) References Cited

OTHER PUBLICATIONS

Institute of Electrical and Electronics Engineers Journal of Solid-State Circuits, vol. 40, No. 3, Mar. 2005, pp. 763-771.
Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.
Jonas et al., "Studies on the Feasibility of Urinary Bladder Evacuation by Direct Spinal Cord Stimulation. I. Parameters of Most Effective Stimulation", Investigative Urology, vol. 13, No. 2, 1975, pp. 142-150.
Kakuta et al., "In Vivo Long Term Evaluation of Transcutaneous Energy Transmission for Totally Implantable Artificial Heart", American Society for Artificial Internal Organs Journal, Mar.-Apr. 2000, pp. 1-2.
Kester et al., "Voltage-to-Frequency Converters", Available Online at: https://www.analog.com/media/cn/training-seminars/tutorials/MT-028.pdf, 7 pages.
Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.
Lewis et al., "Early Clinical Experience with the Rechargeable Cardiac Pacemaker", The Annals of Thoracic Surgery, vol. 18, No. 5, Nov. 1974, pp. 490-493.
Love et al., "Experimental Testing of a Permanent Rechargeable Cardiac Pacemaker", The Annals of Thoracic Surgery, vol. 17, No. 2, Feb. 1, 1974, pp. 152-156.
Love, "Pacemaker Troubleshooting and Follow-up", Clinical Cardiac Pacing, Defibrillation, and Resynchronization Therapy, Chapter 24, 2007, pp. 1005-1062.
Madigan et al., "Difficulty of Extraction of Chronically Implanted Tined Ventricular Endocardial Leads", Journal of the American College of Cardiology, vol. 3, No. 3, Mar. 1984, pp. 724-731.
Meglio, "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.
Meyerson, "Alleviation of Atypical Trigeminal Pain by Stimulation of the Gasserian Ganglion via an Implanted Electrode", Acta Neurochirurgica Supplementum, vol. 30, 1980, pp. 303-309.
Mitamura et al., "Development of Transcutaneous Energy Transmission System", Available Online at https://www.researchgate.net/publication/312810915 Ch. 28, Jan. 1988, pp. 265-270.
Nakamura et al., "Biocompatibility and Practicality Evaluations of Transcutaneous Energy Transmission Unit for the Totally Implantable Artificial Heart System", Journal of Artificial Organs, vol. 27, No. 2, 1998, pp. 347-351.

Nashold et al., "Electromicturition in Paraplegia. Implantation of a Spinal Neuroprosthesis", Archives of Surgery., vol. 104, Feb. 1972, pp. 195-202.
Painter et al., "Implantation of an Endocardial Tined Lead to Prevent Early Dislodgement", The Journal of Thoracic and Cardiovascular Surgery, vol. 77, No. 2, Feb. 1979, pp. 249-251.
Paralikar et al., "A Fully Implantable and Rechargeable Neurostimulation System for Animal Research", 7th Annual International Institute of Electrical and Electronics Engineers Engineering in Medicine and Biology Society, Conference of Neural Engineering, Apr. 22-24, 2015, pp. 418-421.
Perez, "Lead-Acid Battery State of Charge vs. Voltage", Available Online at http://www.rencobattery.com/resources/SOC vs-Voltage.pdf, Aug.-Sep. 1993, 5 pages.
Schaldach et al., "A Long-Lived, Reliable, Rechargeable Cardiac Pacemaker", Engineering in Medicine, vol. 1: Advances in Pacemaker Technology, 1975, 34 pages.
Scheuer-Leeser et al., "Polyurethane Leads: Facts and Controversy", PACE, vol. 6, Mar.-Apr. 1983, pp. 454-458.
Sivaprakasam et al., "A Variable Range Bi-Phasic Current Stimulus Driver Circuitry for an Implantable Retinal Prosthetic Device", Institute of Electrical and Electronics Engineers Journal of Solid-State Circuits, Institute of Electrical and Electronics Engineers Service Center, Piscataway, vol. 40, No. 3, Mar. 1, 2005, pp. 763-771.
Smith, "Changing Standards for Medical Equipment", UL 544 and UL 187 vs. UL 2601 ("Smith"), 2002, 8 pages.
Tanagho et al., "Bladder Pacemaker: Scientific Basis and Clinical Future", Urology, vol. 20, No. 6, Dec. 1982, pp. 614-619.
Tanagho, "Neuromodulation and Neurostimulation: Overview and Future Potential", Translational Androl Urol, vol. 1, No. 1, 2012, pp. 44-49.
Torres et al., "Electrostatic Energy-Harvesting and Battery-Charging CMOS System Prototype", IEEE Transactions on Circuits and Systems I: Regular Papers, vol. 56, No. 9, Dec. 22, 2008, pp. 1938-1948.
Van Paemel, "High-Efficiency Transmission for Medical Implants", Institute of Electrical and Electronics Engineers Solid-State Circuits Magazine, vol. 3, No. 1, Jan. 1, 2011, pp. 47-59.
Wang et al., "A 140-dB CMRR Low-Noise Instrumentation Amplifier for Neural Signal Sensing", Asia-Pacific Conference on Circuits and Systems, Institute of Electrical and Electronics Engineers Asia Pacific Conference, Dec. 1, 2006, pp. 696-699.
Young, "Electrical Stimulation of the Trigeminal Nerve Root for the Treatment of Chronic Facial Pain", Journal of Neurosurgery, vol. 83, No. 1, Jul. 1995, pp. 72-78.
U.S. Appl. No. 14/446,294, filed Jul. 29, 2014.

* cited by examiner

CHARGING DEVICE WITH OFF-CENTER COIL

CROSS-REFERENCES TO RELATED APPLICATIONS

This application claims the benefit of U.S. Provisional Application No. 62/816,829, filed Mar. 11, 2019, and entitled "CHARGING DEVICE WITH OFF-CENTER COIL", the entirety of which is hereby incorporated by reference herein.

FIELD

The present invention relates to neurostimulation treatment systems and associated devices, as well as methods of treatment, implantation and configuration of such treatment systems.

BACKGROUND

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/or voltage that is effective to affect a body function for one patent may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, current stimulation systems rely on recharging of energy storage features such as batteries that are used in generating stimulation of the patient's tissue. Many of the recharging systems utilize wireless power transfer techniques to transcutaneously provide power for recharging the energy storage features. Such wireless power transfer techniques frequently utilize coupling between a charging device external to the patient and a stimulator implanted within the patient. The effectiveness of this coupling can vary based on: the relative position of the charging device with respect to the stimulator; the orientation of the charging device with respect to the stimulator; and/or the distance separating the charging device and the stimulator.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of coupling between the charging device and the implanted stimulator.

BRIEF SUMMARY

One aspect of the present disclosure relates to aspects of an implantable pulse generator and/or charging device, and specifically relate to aspects of power transmission and power receiving features of the implantable pulse generator and/or the charging device. The charging device can include a sending coil assembly that can include a wire winding of a first type. This first type of wire winding can be, for example, a planar wire winding. This planar wire winding can be mounted to a surface of a core of the charging device. This wire winding can be centered on the core of the charging device, or can, in some embodiments, be offset from the center of the core of the charging device. The implantable pulse generator can include a wire winding of a second type. This second type of wire winding can be, for example, an elongate wire winding. The loops forming the elongate wire winding can each wrap around an core that can be an elongate core.

This mismatch of winding types between the charging device and the implantable pulse generator provides several benefits including the enabling of more robust coupling between the charging device and the implantable pulse generator when power is transmitted from the charging device to the implantable pulse generator. Specifically, the use of mismatched winding types can result in a robust coupling that is either insensitive to the orientation of the charging device with respect to the implantable pulse generator and/or that has reduced sensitivity to the orientation of the charging device with respect to the implantable pulse generator.

The core of the charging device can be positioned between the wire winding of the charging device and circuitry of the charging device. This circuitry of the charging device can, for example, control the generation of the magnetic field by the charging device. The core can be designed such that the magnetic field does not extend through the core towards the circuitry, but is rather, the magnetic field is directed in a desired direction. The positioning of the core can focus the magnetic field, and specifically can increase the directionality of the magnetic field. The improved directionality of the magnetic field can further increase the Q-value of the sending coil assembly. Due to the increased directionality and increase Q-value, the number of windings in the sending coil can be decreased, and specifically the diameter of the wire in the windings can be increased as the number of coils decreases. This change in the diameter of the wire in the windings can decrease electrical losses in the sending coil, and can thus increase the efficiency with which the charging device recharges the implantable pulse generator. In some embodiments, the positioning of the core between the wire winding and the circuitry of the charging device can isolate the circuitry from a magnetic field generated via powering of the sending coil assembly. By isolating the circuitry, the efficiency of coupling is improved as energy is not lost in the inducing of current within the circuitry and/or in the heating of the circuitry. This not only increases efficiency of coupling between the charging device and the implantable pulse generator, but also decreases risks associated with heating of the charging device during transmission of power to the implantable pulse generator.

One aspect of the present disclosure relates to a neurostimulation system for delivering one or more electrical pulses to a target region within a patient's body. The system includes an implantable neurostimulator for delivering the one or more electrical pulses. The implantable neurostimulator includes a hermetic housing made of a biocompatible material, an energy storage feature that can power the implantable neurostimulator, a receiving coil assembly including an elongate wire winding wound around a first ferritic core, and control circuitry configured to control recharging of the energy storage feature. The system can include a charging device for wirelessly delivering energy to the implantable neurostimulator. The charging device can include a sending coil assembly including a planar wire winding coupled to a surface of a second ferritic core.

In some embodiments, the elongate wire winding extends parallel to a central axis of the first ferritic core. In some embodiments, a winding axis of the planar wire winding is parallel to a core axis of the second ferritic core. In some embodiments, the planar wire winding and the second ferritic core are coaxial, and in some embodiments, the planar wire winding and the second ferritic core are non-coaxial.

In some embodiments, the planar wire winding has a winding axis along the centerline of the planar wire winding. In some embodiments, the second ferritic core has a core axis along the centerline of the second ferritic core. In some embodiments, the core axis is perpendicular to the surface of the second ferritic core. In some embodiments, the winding axis of the planar wire winding is laterally offset with respect to the core axis of the second ferritic core. In some embodiments, the winding axis and the core axis are parallel.

In some embodiments, the charging device further includes charging circuitry for controlling powering of the sending coil assembly to generate a magnetic field to transfer power to the implantable neurostimulator. In some embodiments, the second ferritic core is positioned between the planar wire winding and the charging circuitry. In some embodiments, the second ferritic core isolates the charging circuitry from the magnetic field. In some embodiments, the charging circuitry is isolated from the magnetic field via the second ferritic core. In some embodiments, the second ferritic core is a disk, and in some embodiments, the first ferritic core is a rod.

One aspect of the present disclosure relates to a method of charging an implantable neurostimulator with a charging device. The method includes positioning a charging device adjacent to an implantable neurostimulator and generating a magnetic field via powering of a sending coil assembly of the charging device. In some embodiments, the implantable neurostimulator includes a receiving coil assembly. In some embodiments, the sending coil assembly includes a planar wire winding coupled to a surface of a second ferritic core. In some embodiment charging circuitry of the charging device is isolated from the magnetic field by the second ferritic core.

In some embodiments, the second ferritic core is positioned between the planar wire winding and the charging circuitry. In some embodiments, the planar wire winding is centered on the surface of the second ferritic core, and in some embodiments, the planar wire winding is off-center on the surface of the second ferritic core.

In some embodiments, the receiving coil assembly comprises an elongate wire winding wound around a first ferritic core. In some embodiments, the elongate wire winding extends parallel to a central axis of the first ferritic core, and a winding axis of the planar wire winding is parallel to a core axis of the second ferritic core. In some embodiments, when the charging device is positioned adjacent to the implantable neurostimulator, the central axis of the first ferritic core is non-parallel to the winding axis of the planar wire winding. In some embodiments, when the charging device is positioned adjacent to the implantable neurostimulator, the central axis of the first ferritic core is perpendicular to the winding axis of the planar wire winding.

One aspect of the present disclosure relates to a neurostimulation system for delivering one or more electrical pulses to a target region within a patient's body. The system includes an implantable neurostimulator. The implantable neurostimulator includes an energy storage feature for powering the implantable neurostimulator and an elongate receiving coil assembly. The system includes a charging device for wirelessly delivering energy to the implantable neurostimulator. The charging device includes a sending coil assembly having a planar wire winding coupled to a surface of a ferritic core.

In some embodiments, the planar wire winding is centered on the surface of the ferritic core, and in some embodiments, the planar wire winding is off-center on the surface of the ferritic core. In some embodiments, the charging device includes charging circuitry for controlling powering of the sending coil assembly to generate a magnetic field to transfer power to the implantable neurostimulator. In some embodiments, the ferritic core is positioned between the charging circuitry and the planar wire winding. In some embodiments, the ferritic core is designed to isolate the charging circuitry from the magnetic field. In some embodiments, the ferritic core comprises a disk. In some embodiments, the elongate receiving coil assembly includes an elongate wire winding wound around an elongate ferritic core.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
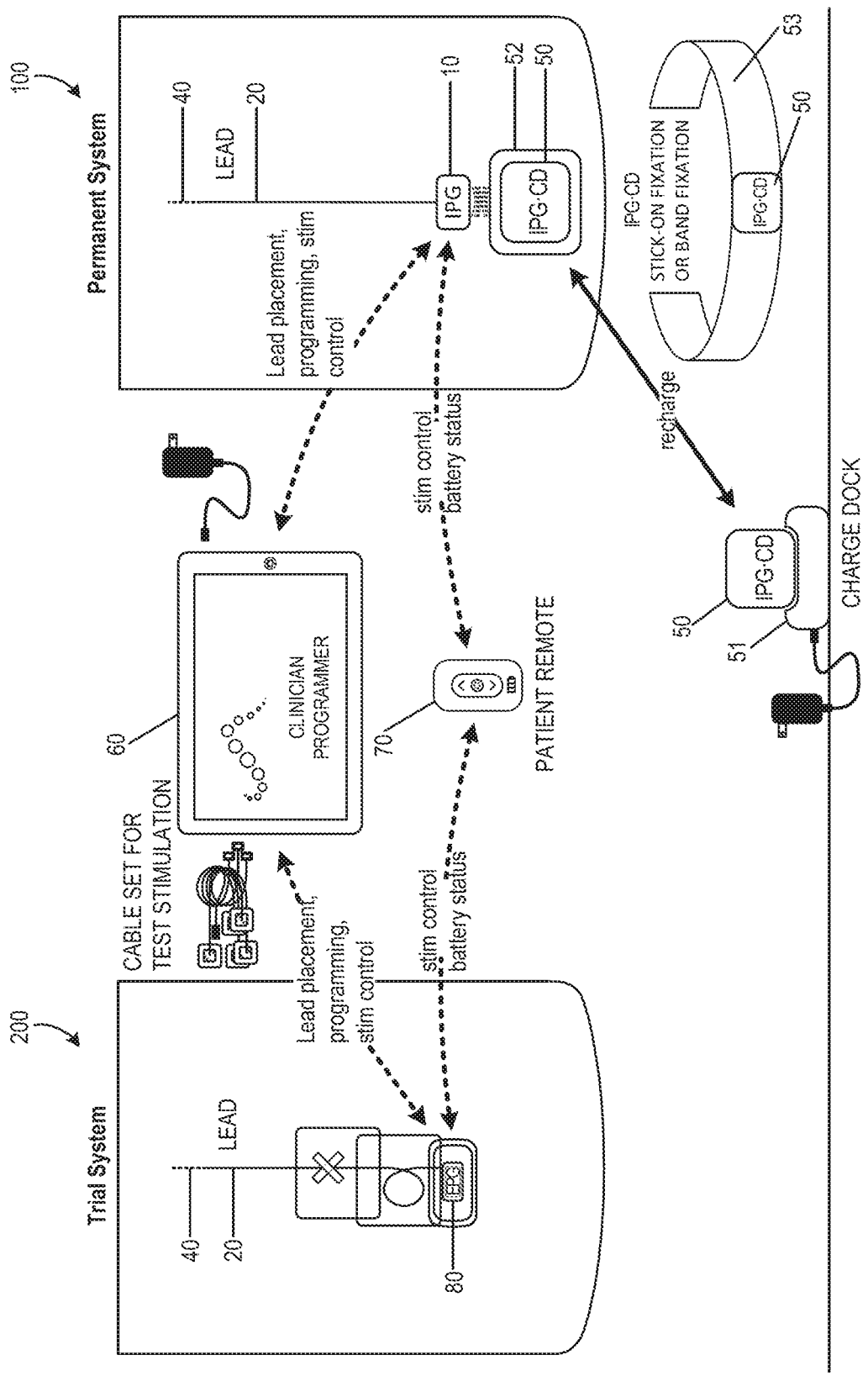
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. It will be appreciated, however, that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include life-style modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number of randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies; however, long-term safety and effectiveness of PTNS are relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, are supported by multiple studies and are well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
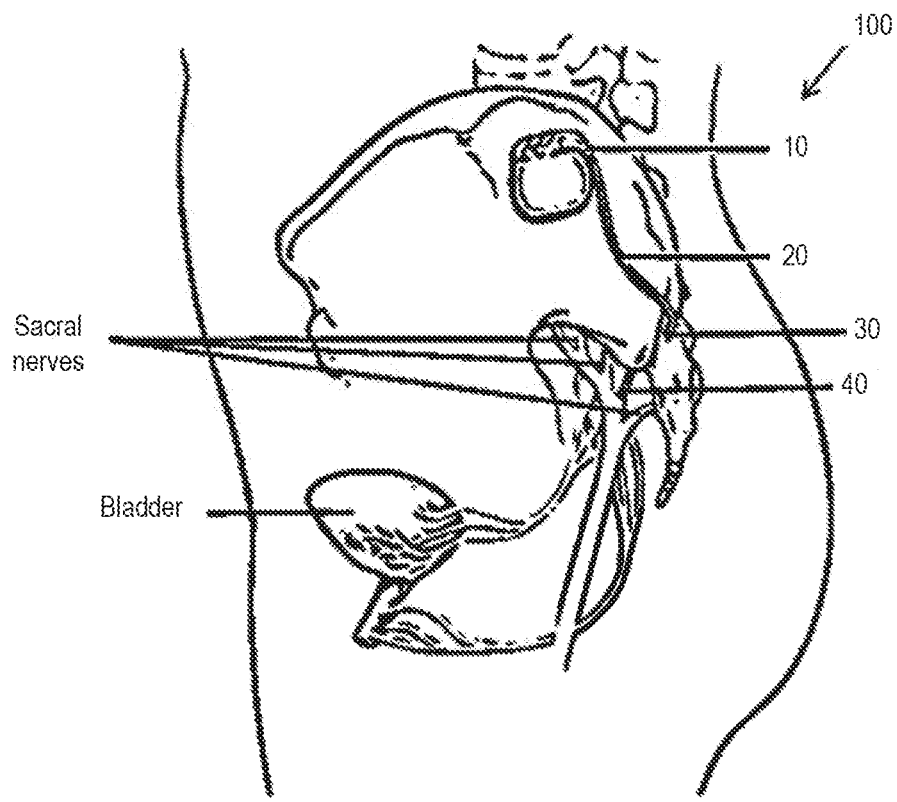
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| Nerve Innervation | Response | | |
|---|---|---|---|
| | Pelvic Floor | Foot/calf/leg | Sensation |
| S2 Primary somatic contributor of pudendal nerve for external sphincter, leg, foot | "clamp"* of anal sphincter" | Leg/hip rotation, plantar flexion of entire foot, contraction of calf | Contraction of base of penis, vagina |
| S3 Virtually all pelvic autonomic functions and striated muscle (levator ani) | "bellows"** of perineum | Plantar flexion of great toe, occasionally other toes | Pulling in rectum, extending forward to scrotum or labia |
| S4 Pelvic autonomic and somatic No leg or foot | "bellows"** | No lower extremity motor stimulation | Pulling in rectum only |

*Clamp contraction of anal sphincter and, in males, retraction of base of penis. Move buttocks aside and look for anterior/posterior shortening of the perineal structures.
**Bellows: sitting and dropping of pelvic floor. Look for deepening and flattening of buttock grove.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex.

This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupts, inhibits, or prevents neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract), in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measurable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
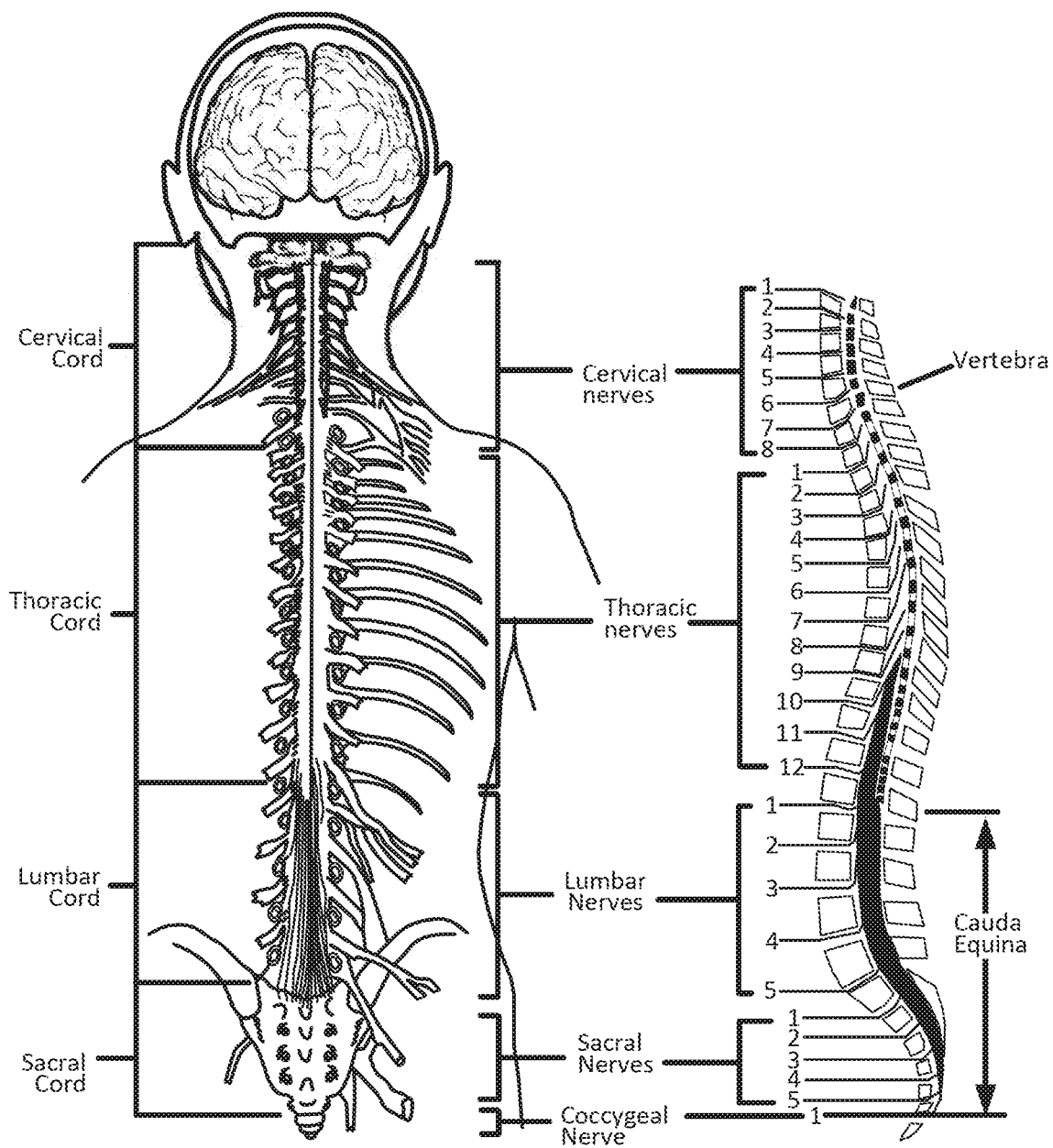
FIGS. 2A-2C show diagrams of the nerve structures along the spine, the lower back and sacrum region, which may be stimulated in accordance with aspects of the invention.
Figure 2B:
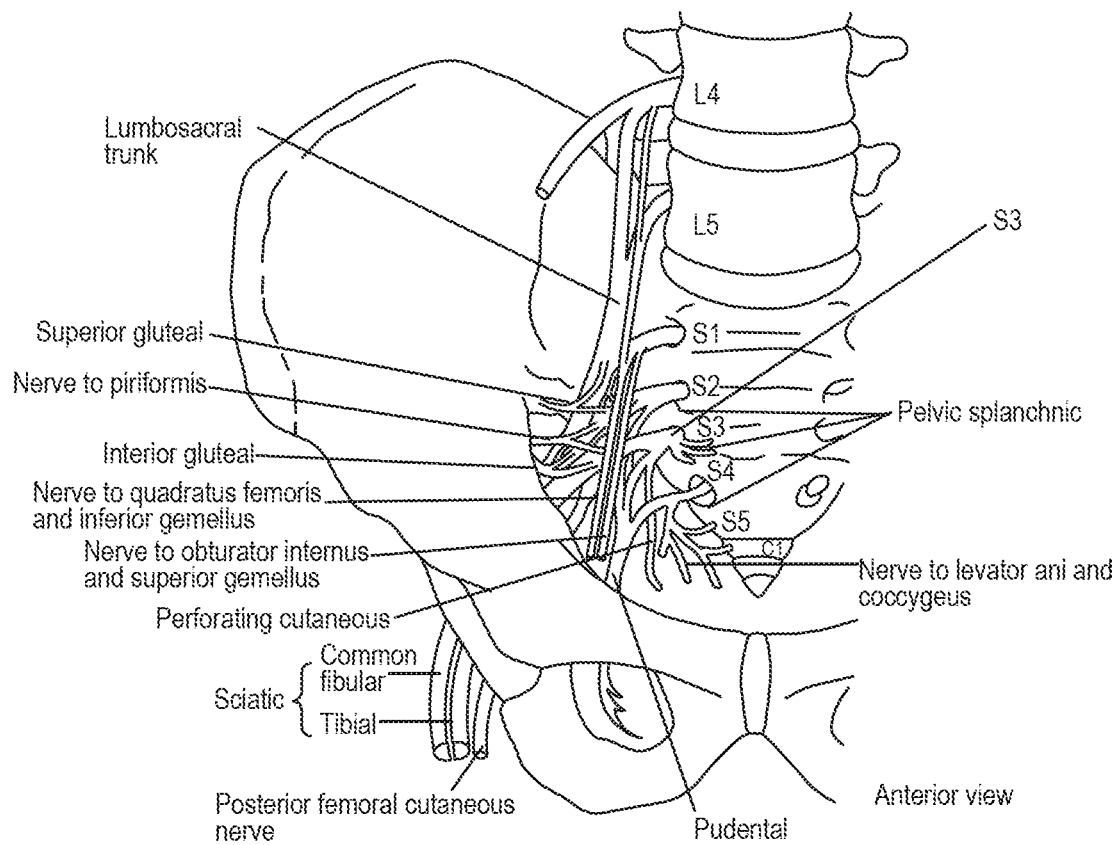
Figure 2C:
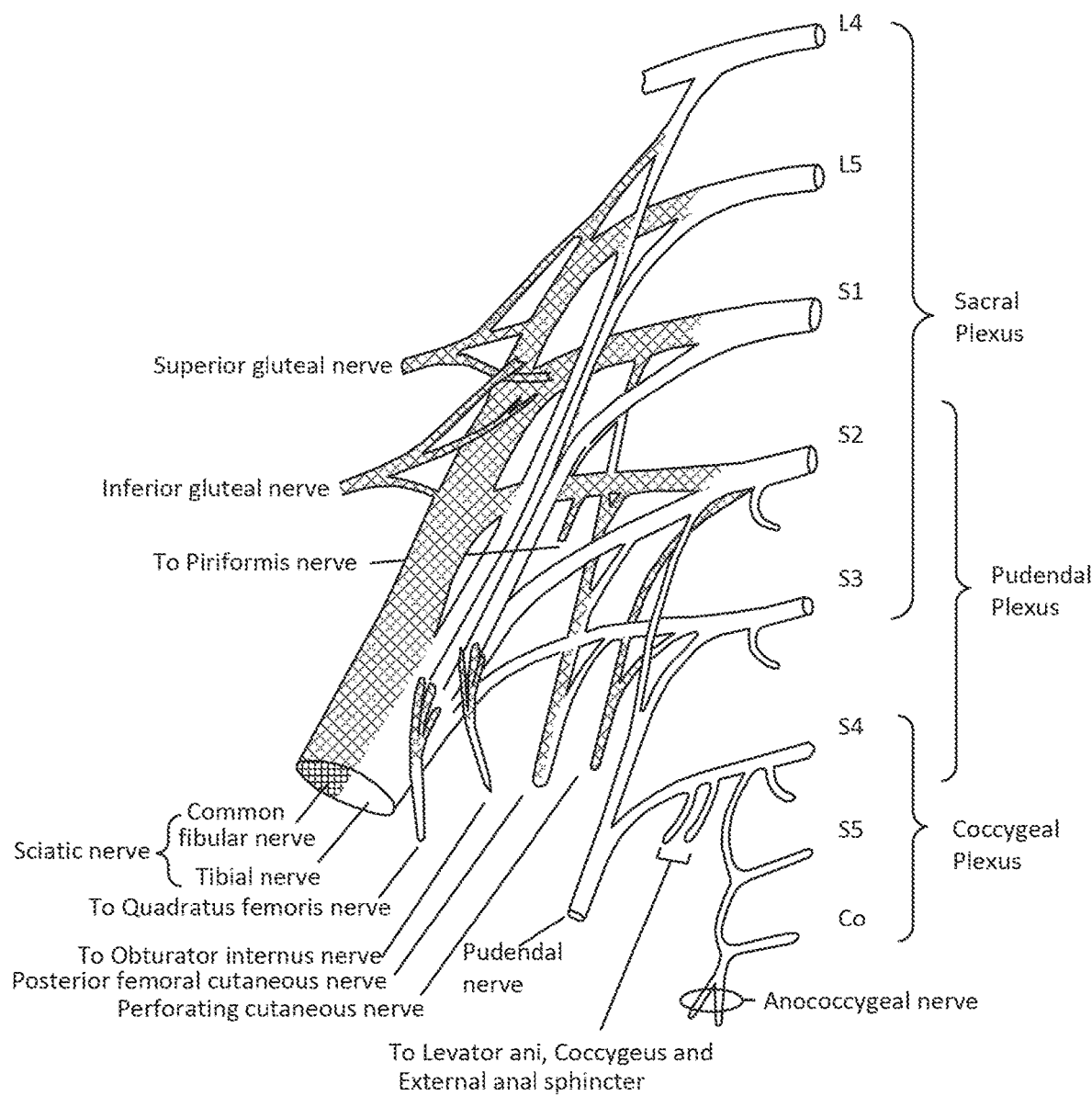

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder-related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
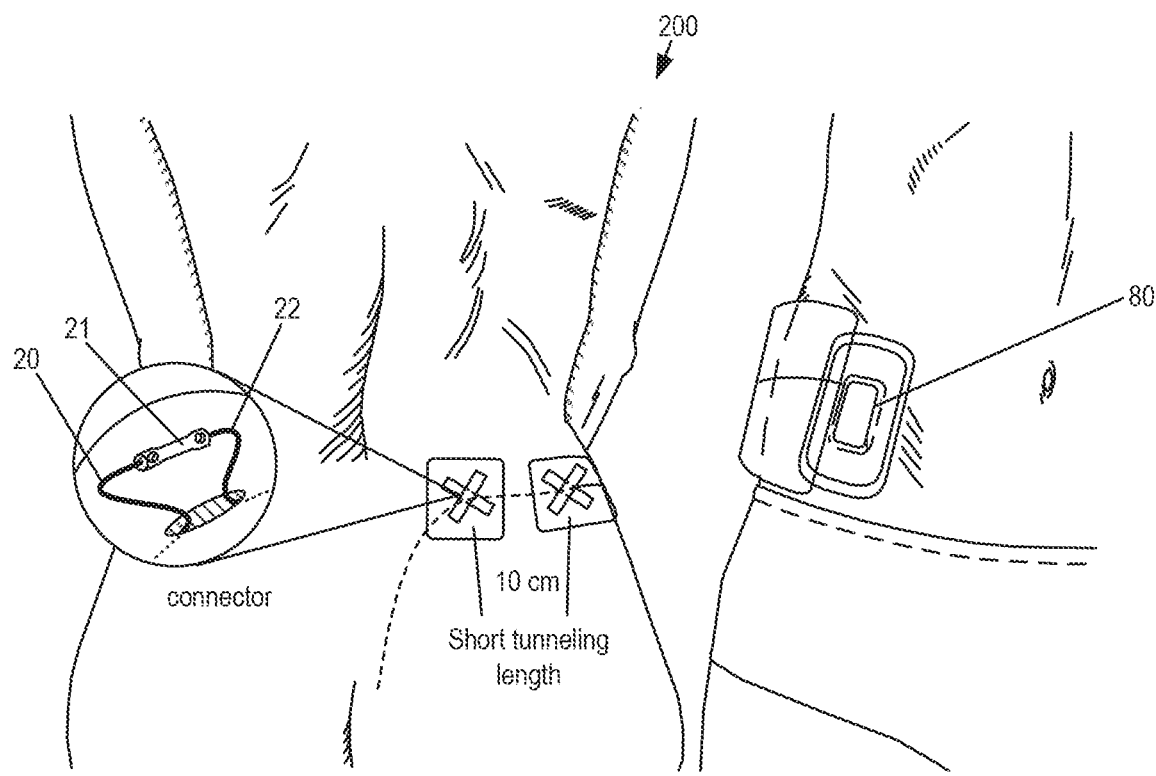
FIG. 3B shows an example of a neurostimulation system having a partly implanted stimulation lead and an external pulse generator adhered to the skin of the patient for use in a trial stimulation, in accordance with aspects of the invention.
Figure 3B:
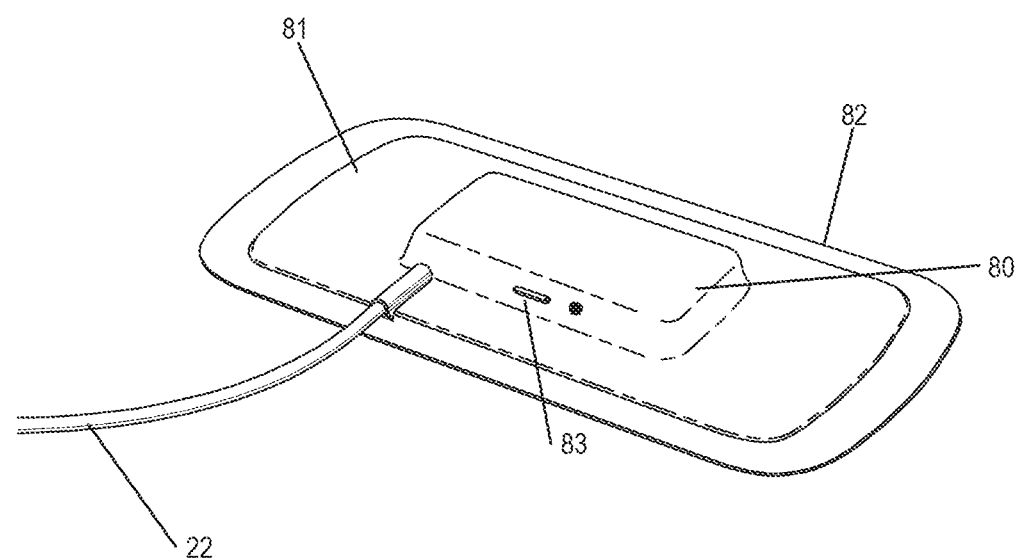

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) therebetween. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which includes an aperture or port through which the EPG 80 is connected to the lead extension 22. The patch may further include an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
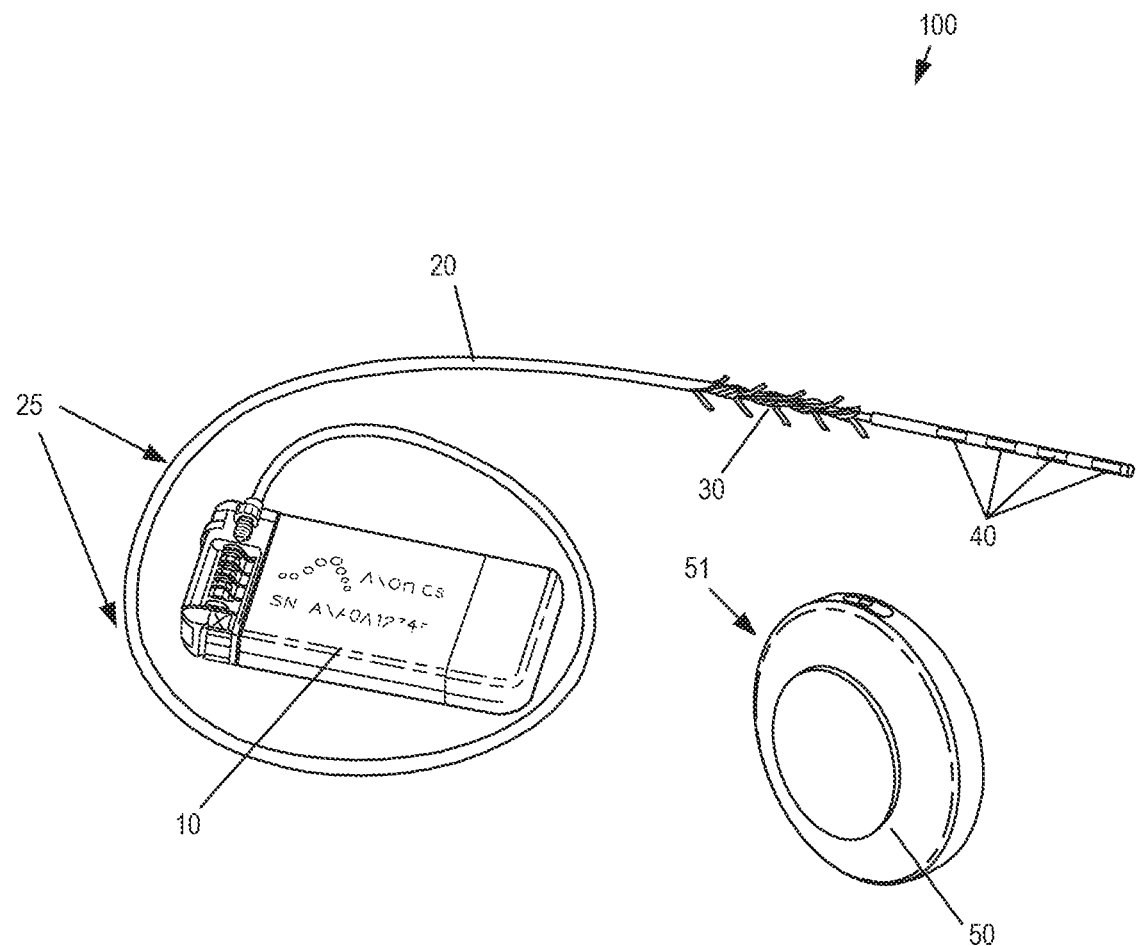
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD 50 is used for transcutaneous charging of the IPG through RF induction. The CD 50 can either be either patched to the patient's skin using an adhesive or can be held in place using a belt 53 or by an adhesive patch 52. When recharging the IPG 10, the CD 50 can be held in place using the belt 53 or adhesive patch 52 such that a surface 54 of the CD 50 contacts the skin through which the IPG 10 is recharged, is parallel to the skin through which the IPG 10 is recharged, and/or is proximate to the skin through which the IPG 50 is recharged. In such position, the CD axis 55, which can be perpendicular to the surface 54 can be perpendicular to the skin through which the IPG 10 is recharged. The CD 50 may be charged by plugging the CD directly into an outlet or by placing the CD in a charging dock or station 51 that connects to an AC wall outlet or other power source.

The CD 50 can include a housing 51. The housing 51 can comprise a variety of shapes and sizes. In some embodiments, the housing 51 can be cylindrically shaped as shown in FIG. 4, and specifically, can comprise a plurality of connected cylindrical portions, wherein the connected cylindrical portions have different diameters and/or lengths. In some embodiments, the housing 51 can be a metal or polymer such as a plastic or the like.

The CD 50 can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. The CD 50 may include an energy storage feature, such as one or more capacitors, and typically includes a wireless charging unit. Some details of CD 50 will be discussed at greater lengths below with respect to FIG. 7.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
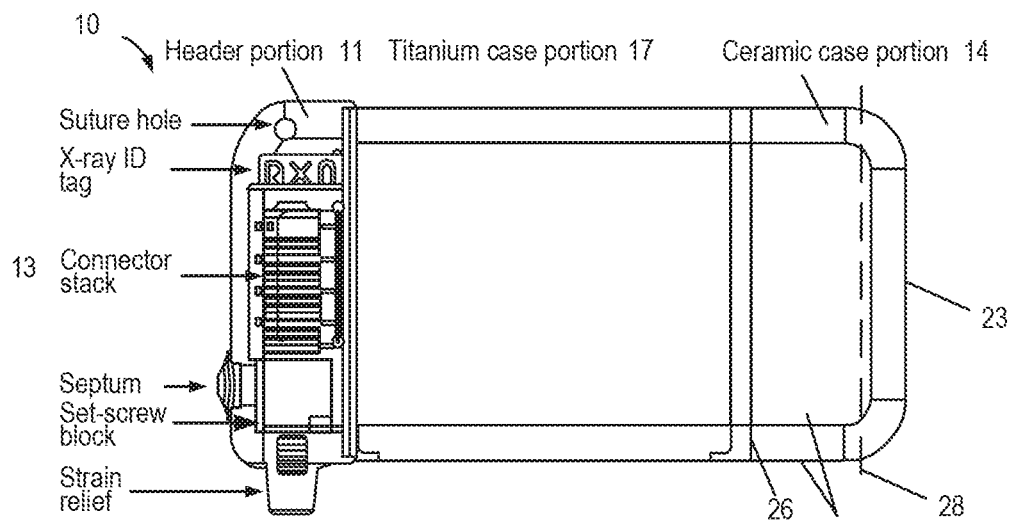
FIGS. 5A-5C show detail views of an implantable pulse generator and associated components for use in a neurostimulation system, in accordance with aspects of the invention.
Figure 5B:
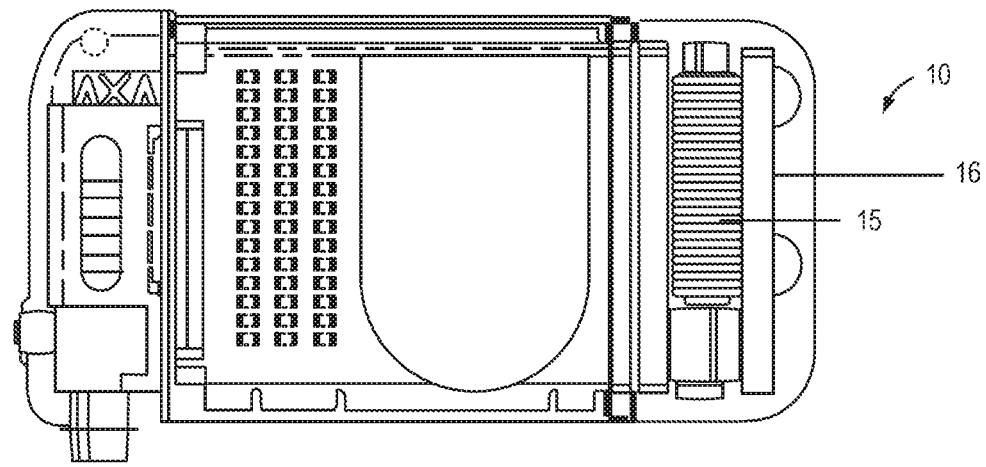
Figure 5C:
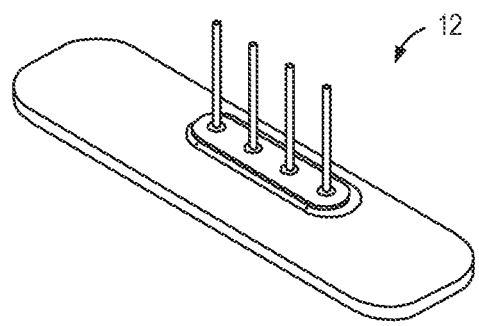

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed-through assembly 12 and connector stack 13, while the ceramic case portion 14 houses an antennae assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. The ceramic portion 14 includes an end 23, sides 24, and a connection portion 26 that connects the ceramic portion 14 to the case portion 17. In the example shown in FIG. 5B, the antennae assembly 16 is positioned such that a plane 28, in which loops of a radiating element lay, is perpendicular to and extends through the sides 24 of the ceramic portion 14.

In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. In some embodiments, some or all of the pieces of the IPG 10 forming the hermetic housing can be biocompatible, and specifically, can have external surfaces made of biocompatible materials.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at a depth of 3 cm with the CD, when positioned on a skin surface of the patient near the IPG, and reduces re-charging time.

Figure 6:
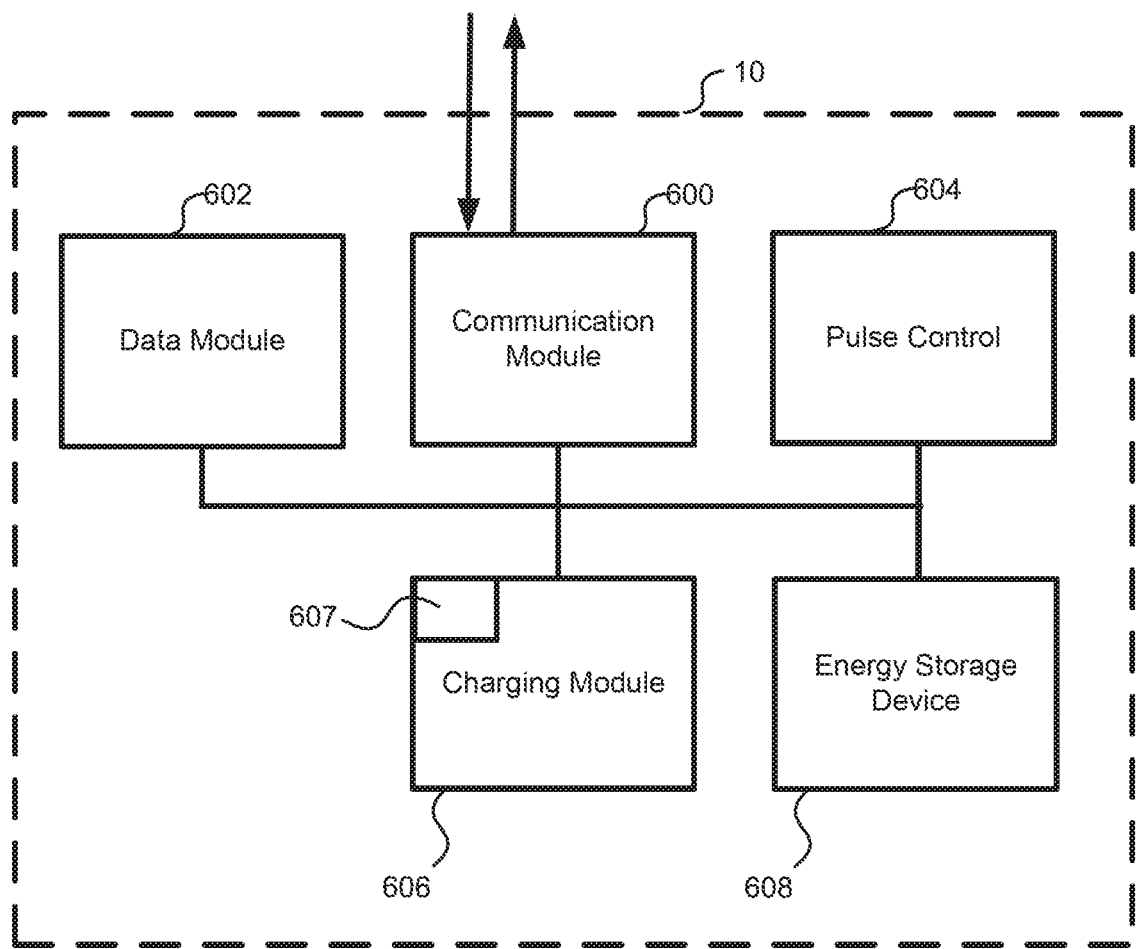
FIG. 6 shows a schematic illustration of one embodiment of the architecture of the IPG.

FIG. 6 shows a schematic illustration of one embodiment of the architecture of the IPG 10. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 can be located within the housing.

In some embodiments, the IPG 10 can include, for example, a communication module 600. The communication module 600 can be configured to send data to and receive data from other components and/or devices of the exemplary nerve stimulation system including, for example, the clinician programmer 60, the charging device 50, and/or the patient remote 70. In some embodiments, the communication module 600 can include one or several antennas and software configured to control the one or several antennas to send information to and receive information from one or several of the other components of the IPG 10. In some embodiments, for example, when connecting with the charging device 50, the communications module 600 can be configured to send data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of a charging module 606 of the IPG 10 and/or of one or several components of the charging module 606 of the IPG.

The IPG 10 can further include a data module 602. The data module 602 can be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like. In some embodiments, the information associated with the property of the IPG 10 can include, for example, data identifying the natural frequency of the IPG 10 and/or components thereof. In some embodiments, this information identifying the natural frequency can be generated at the time of the manufacture of the IPG 10.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 can be stored within the memory.

The IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charging device 50 to create an inductive coupling to thereby recharge the IPG 10. In some embodiments, the charging module 606 can include hardware and/or software configured to monitor the charging of the IPG 10 including, for example, the charging coil assembly 15, also referred to herein as the receiving coil assembly 15 or the elongate receiving coil assembly 15.

The charging module 606 of the IPG 10 can include a charging circuit 607, also referred to herein as the resonant circuit 607, the secondary charging circuit 607, the secondary resonant circuit 607, the receiving charging circuit 607, or the receiving resonant circuit 607. In some embodiments, the charging circuit 607 can comprise, for example, at least one of: an inductor; a capacitor; or a resistor. The charging circuit 607 can be characterized by a natural frequency, which natural frequency can be determined at, for example, the time of assembly of the charging circuit 607 or after the implantation of the IPG 10 in the body. In some embodiments, because of the relatively constant temperature and environment in the body, the natural frequency of the charging circuit 607 can remain constant after the implantation of the IPG 10 into the body.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
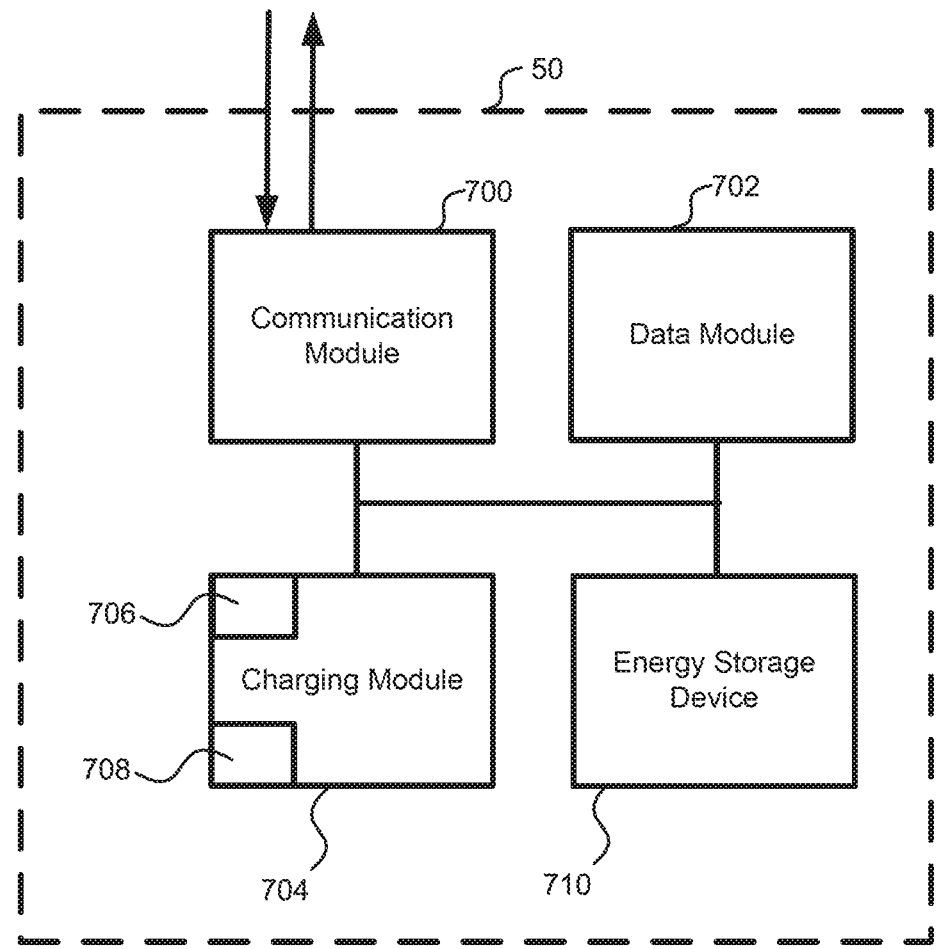
FIG. 7 shows a schematic illustration of one embodiment of the architecture of the charging device.

FIG. 7 shows a schematic illustration of one embodiment of the architecture of the charging device 50. In some embodiments, each of the components of the architecture of the charging device 50 can be implemented using the processor, memory, and/or other hardware component of the charging device 50. In some embodiments, the components of the architecture of the charging device 50 can include software that interacts with the hardware of the charging device 50 to achieve a desired outcome, and the components of the architecture of the charging device 50 can be located within the housing 51.

In some embodiments, charging device 50 can include, for example, a communication module 600. The communication module 700 can be configured to send data to and receive data from other components and/or devices of the exemplary nerve stimulation system including, for example, the clinician programmer 60, the IPG 10, and/or the patient remote 70. In some embodiments, the communication module 700 can include one or several antennas and software configured to control the one or several antennas to send information to and receive information from one or several of the other components of the CD 50. In some embodiments, for example, when connecting with the IPG 10, the communications module 700 can be configured to receive data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of the charging module 606 of the IPG 10 and/or of one or several components of the charging module 606 of the IPG.

The CD 50 can further include a data module 702. The data module 702 can be configured to manage data relating to the identity and properties of the IPG 10. In some embodiments, the data module can include one or several database that can, for example, include information relating to the IPG 10 such as, for example, the identification of the IPG 10, one or several properties of the IPG 10, or the like. In one embodiment, for example, the data module can comprise a database including one or several IPG 10 identifiers such as serial numbers for those one or several IPGs 10. In some embodiments, the data module 702 can further include characterization data associated with some or all of the one or several IPGs 10 identified in the data module 702. In some embodiments, for example, this characterization data can include the identification of the natural frequency of charging circuit 607 of the IPG 10. In some embodiments, this characterization data can be received from the IPG 10 and/or can be generated by the CD 50 in response to interactions with the IPG 10.

The CD 50 can include a charging module 704. In some embodiments, the charging module 704 can be configured to control and/or monitor the charging/recharging of the IPG 10. In some embodiments, for example, the charging module 704 can include one or several features configured to provide energy for recharging the IPG 10 such as, for example, one or several inductive coils/features that can interact with one or several inductive coils/features of the IPG 10 to create an inductive coupling to thereby recharge the IPG 10. In some embodiments, the charging module 704 can include hardware and/or software configured to monitor the charging of the IPG 10 including, for example, the charging coil assembly 15.

The charging module 704 of the CD 50 can include a charging circuit 706, also referred to herein as the resonant circuit 706, the primary charging circuit 706, the primary resonant circuit 706, the transmitter charging circuit 706, or the transmitter resonant circuit 706. In some embodiments, the charging circuit 706 can comprise, for example, at least one of: an inductor; a capacitor; or a resistor. In some embodiments, the resonant circuit 706 can comprise the sending coil assembly, also referred to herein as a transmitting coil assembly or a primary coil assembly.

In some embodiments, the charging module 704 can include a driver 708. The driver 708 can be, for example, a non-class E driver, and in some embodiments, the driver 708 can be a class E driver, and specifically can be a microprocessor controlled class E driver as disclosed in U.S. patent application Ser. No. 14/446,294, filed on Jul. 29, 2014, the entirety of which is hereby incorporated by reference herein. In some embodiments, the driver 708 can be configured to provide electrical pulses to the resonant circuit 706 to thereby charge the IPG 10. In some embodiments, the driver 708 can be further configured to provide these pulses at a frequency corresponding to the natural frequency of the resonant circuit 706. Thus, in some embodiments, the natural frequency of the resonant circuit 706 of the CD 50 can be determined by determining the frequency with which the driver 708 is providing pulses to the resonant circuit 706.

The CD 50 can include an energy storage device 710. The energy storage device 710 can be any device and/or features configured to store energy and can include, for example, one or several batteries, capacitors, fuel cells, or the like. In some embodiments, the energy storage device 710 can be configured to provide charging energy to the charging module 704 for charging of the IPG 10.

Figure 8:
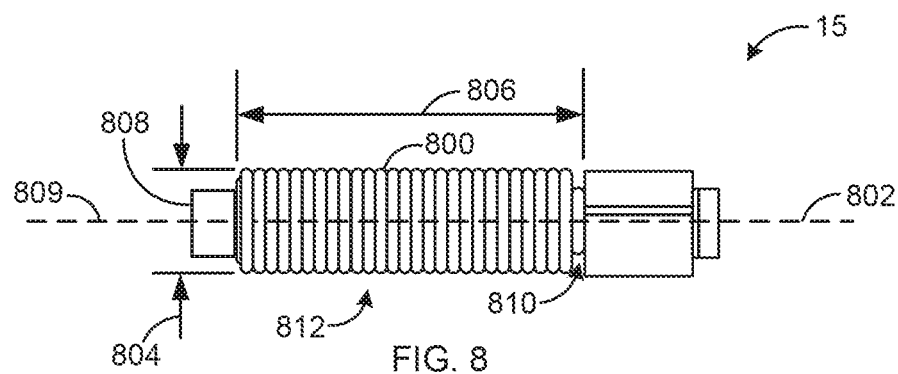
FIG. 8 shows a schematic illustration of one embodiment of the charging coil assembly.

FIG. 8 shows a schematic illustration of one embodiment of the charging coil assembly 15. The charging coil assembly 15 includes a wire winding 800. The wire forming the wire winding 800 can be litz wire. The wire winding 800 can wind around a central axis 802. The wire winding 800 can have a width and/or diameter 804 measured perpendicular to the central axis 802 and a length 806 measured parallel to the central axis 802. The wire winding 800 can be an elongate winding with the length 806 greater than the width and/or diameter 804.

The wire winding 800 can be wound around a core 808 which can be a rod, an elongate core, and/or rod shaped core. The core 808 can comprise a ferritic core, and in some embodiments, the core 808 can be made of a soft ferrite material. The core 808 can comprise a central axis 809, which central axis 809 can extend along a centerline of the core 808.

In some embodiments, the IPG 10 can be implanted such that the central axis 802 of the wire winding 800 and/or the central axis 809 of the core 808 can be parallel and/or substantially parallel with a skin surface closest to the IPG 10 and/or from which charging of the IPG 10 is intended. In some embodiments, the central axis 802 of the wire winding 800 and/or the central axis 809 of the core 808 is substantially parallel with the skin surface when the angle between at least one of the axes 802, 809 and the skin surface is less than 5 degrees, less than 10 degrees, less than 20 degrees, less than 30 degrees, or less than any other or intermediate value.

The wire winding 800 can comprise a plurality of wire loops around the central axis 802 of the charging coil assembly 15. In some embodiments, the wire winding 800 extends parallel to the central axis 809 of the core 808 and/or extends along a portion of the central axis 809 of the core 808. The wire winding 800 can comprise any desired number of loops of wire, and can, for example, comprise 2 loops, 5 loops, 10 loops, 15 loops, 20 loops, 25 loops, 29 loops, 30 loops, 35 loops, 40 loops, 50 loops 100 loops, 200 loops, 1,000 loops, and/or any other or intermediate number of loops.

In some embodiments, the wire winding can comprise a single layer of loops, and in some embodiments the wire winding 800 can comprise multiple layers of loops such that one layer of loops is on top of another layer of loops. In the embodiment of FIG. 8, the wire winding 800 comprises a first layer 810 of loops and a second layer 812 of loops. As seen in FIG. 8, the second layer 812 of loops overlays the first layer 810 of loops such that the first layer 810 of loops is positioned between the core 808 and the second layer 812 of loops.

Figure 9:
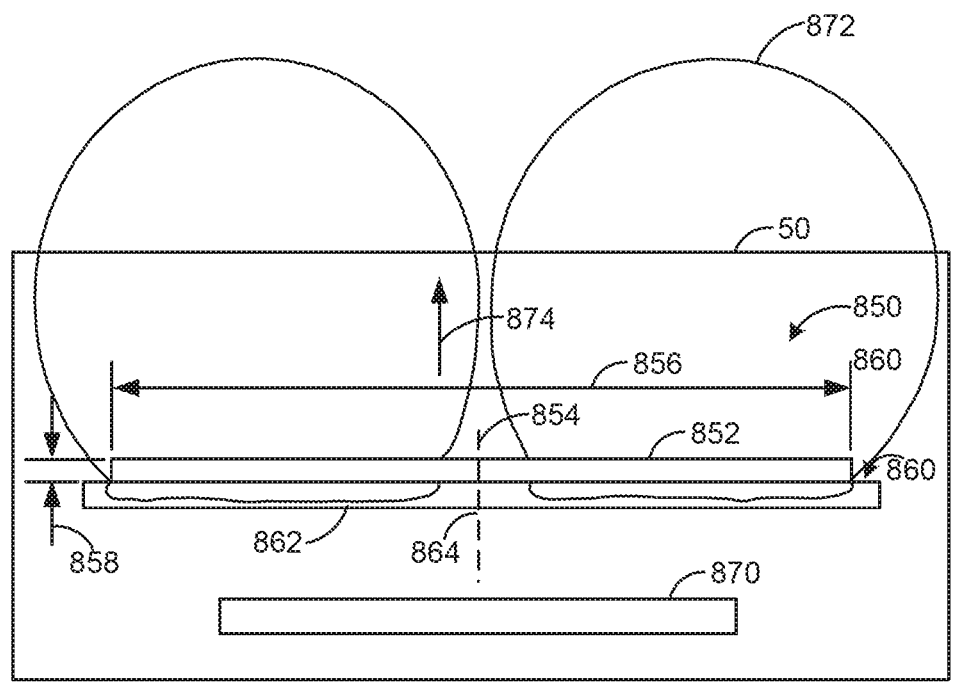
FIG. 9 shows a side view of one embodiment of components of the charging device.

FIG. 9 shows a side view of one embodiment of components of the CD 50. As seen, the CD 50 includes a sending coil assembly 850. The transmitting coil assembly 850 can include a wire winding 852 comprising a plurality of wire loops. The wire forming the wire winding 852 can be litz wire. The wire winding 852 can, in some embodiments, wind around a winding axis 854, which winding axis 854 can extend along the centerline of the wire winding 852. The wire winding 852 can have a width and/or diameter 856 measured perpendicular to the winding axis 854 and a length and/or height 858 measured parallel to the winding axis 854. The wire winding 852 can be a planar winding and/or a pancake winding. As seen in FIG. 9, the width 856 of the wire winding 852 is greater than the height 858.

The wire winding 852 can be positioned on and/or coupled to a surface 860 of a core 862. The core 862 can comprise a ferritic core, and in some embodiments, the core 862 can be made of a soft ferrite material. The wire winding 852 can comprise a plurality of wire loops around the winding axis 854 of the transmitting coil assembly 850. The wire winding 852 can comprise any desired number of loops of wire, which loops can be radial loops and/or longitudinal loops.

Figure 10:
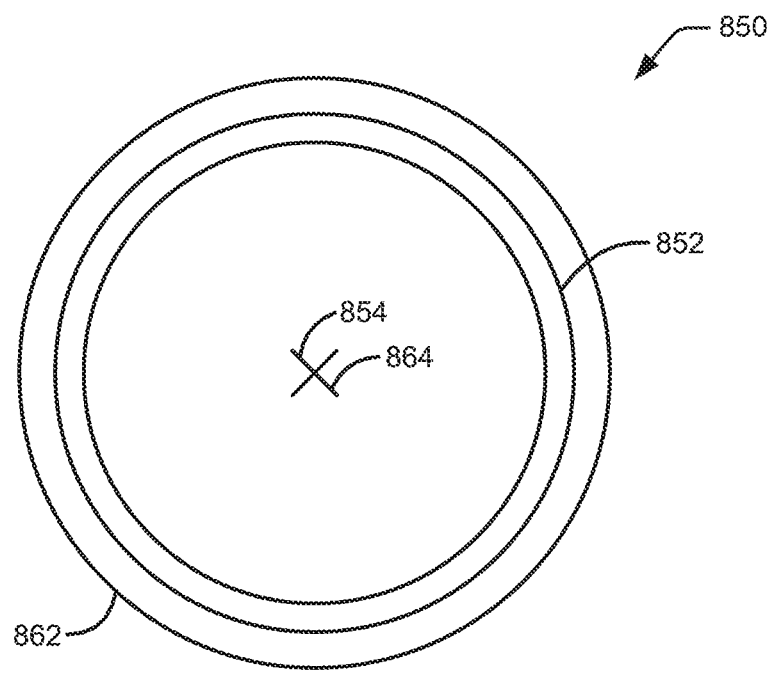
FIG. 10 shows a top view of the transmitting coil assembly with a centered winding.

The core 862 can comprise a core axis 864, which can extend along a centerline through the core 862 and can be perpendicular to the surface 860 of the core 862. In some embodiments, and as seen in FIG. 10, a top view of the transmitting coil assembly 850, in some embodiments, the wire winding 852 can be centered on the surface 860 of the core 862 such that the winding axis 854 overlays the core axis 864, such that the winding axis 854 is coaxial with the core axis 864, and/or such that the winding 852 is coaxial with the core 862. In some embodiments, the wire winding can be positioned on the surface 860 of the core 862 such that the winding axis 854 is parallel to the core axis 864 of the core 862, and in some embodiments, the wire winding can be positioned on the surface 860 of the core 862 such that the winding axis 854 is non-parallel to the core axis 864 of the core 862. In some embodiments, when in the housing 51 of the CD, one or both of the winding axis 854 and/or the core axis 864 can be parallel to the CD axis 55 and/or can be co-axial with the CD axis 55.

The core 862 can comprise a single, solid core, in other words, the core can comprise a monolithic core. In some embodiments, the monolithic core 862 can be seamless and/or can have no magnetic breaks. In some embodiments, the core 862 can have a high permeability. In some embodiments, for example, this permeability can be at least 1,000 at 25° C., at least 2,000 at 25° C., at least 3,000 at 25° C., at least 4,000 at 25° C., or at least any other desired or intermediate number. In some embodiments, this high permeability can create maximum inductance with a minimum amount of current. In some embodiments, this high permeability of the core and seamless design can allow generation of magnetic fields with fewer wire loops. In space limited applications, a decrease in the number of needed wire loops to achieve a desired magnetic allows the use of thicker wire in that same space. In some embodiments, the use of thicker wire can decrease heat dissipated by the wire winding 852 and/or can reduce electrical losses due to resistance of the wire in the wire windings 852. In some embodiments, the use of a seamless, monolithic core can increase the Q value of the sending coil assembly 850. Thus, in some embodiments, the transmitting coil assembly 850 can, in combination with the monolithic core 862, more efficiently transfer energy to an implanted medical device and can recharge more deeply implanted medical devices.

Figure 11:
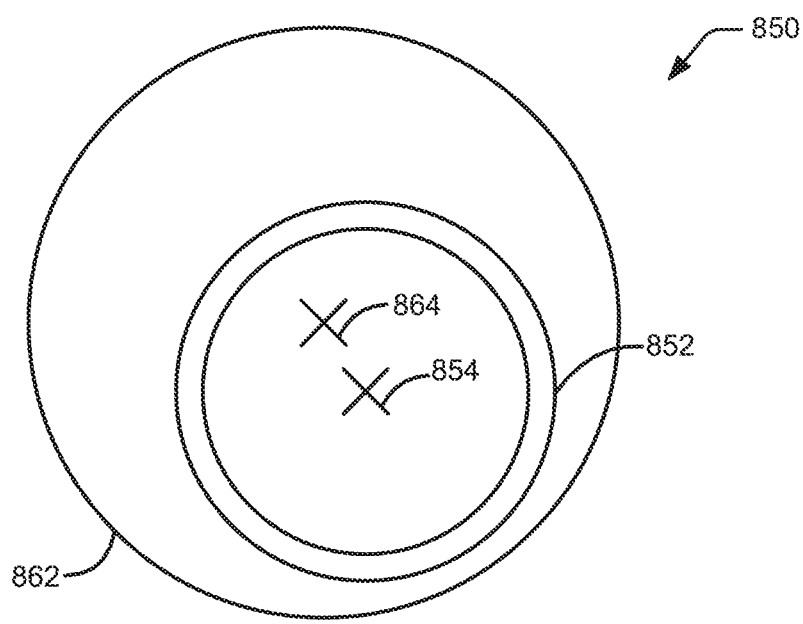
FIG. 11 shows a top view of the transmitting coil assembly with an off-set winding.

As seen in FIG. 11, a top view of another embodiment of the transmitting coil assembly, in some embodiments, the wire winding 852 can be off-centered on the surface 860 of the core 862 with respect to the core 862. In such an embodiment, the winding axis 854 is offset from the core axis 864, and specifically, the winding axis 854 is laterally offset from the core axis 864. As seen in FIG. 11, in some embodiments, the core 862 can comprise a disk.

With reference again to FIG. 9, the CD 50 includes circuitry 870, which can include charging circuitry. This circuitry 870 can include circuitry embodying some or all of the modules of the CD 50 shown in FIG. 7 including, for example, the communication module 700, the data module 702, the charging module 704, and/or the energy storage device 710. In some embodiments, this circuitry 870 can power the sending coil assembly 850 to generate a magnetic field 872. Via this magnetic field, the CD 50 can couple with the IPG 10, and specifically with the charging coil assembly 15 to transfer power to the IPG 10.

In some embodiments, and as seen in FIG. 9, the core 862 can be positioned between the wire winding 852 and the circuitry. In some embodiments, the core 862 can be configured to isolate the charging circuitry 870 from the magnetic field 872. In some embodiments, the core 862 can be further configured to direct the magnetic field in a desired direction indicated by arrow 874. In some embodiments, and as depicted in FIG. 9, the desired direction is parallel to the direction of extension of the core axis 864 and/or of the winding axis 854. As seen in FIG. 9, the field lines of the magnetic field do not extend beyond the core 862 towards the circuitry 870.

Figure 12:
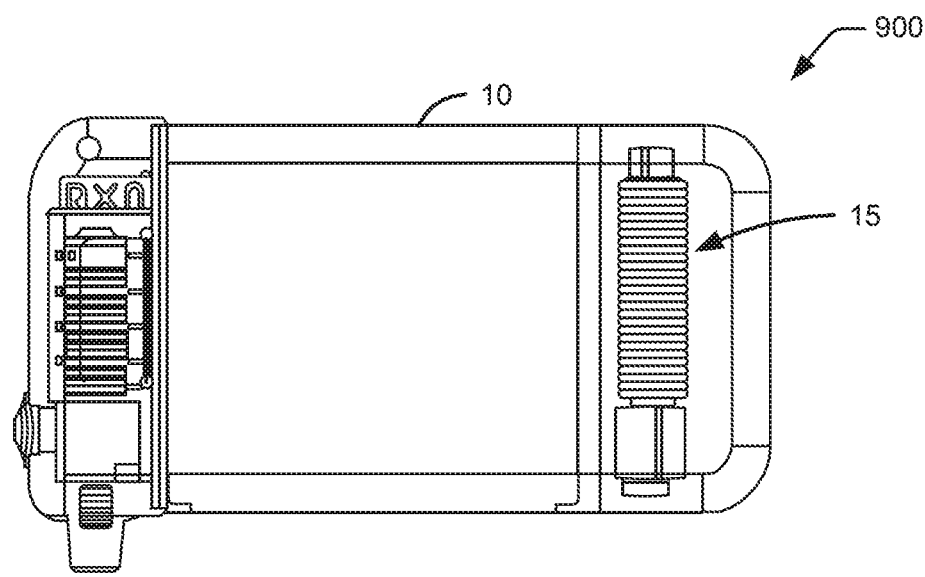
FIG. 12 shows a depiction of one embodiment of charging of an implantable pulse generator via the charging device.
Figure 12:
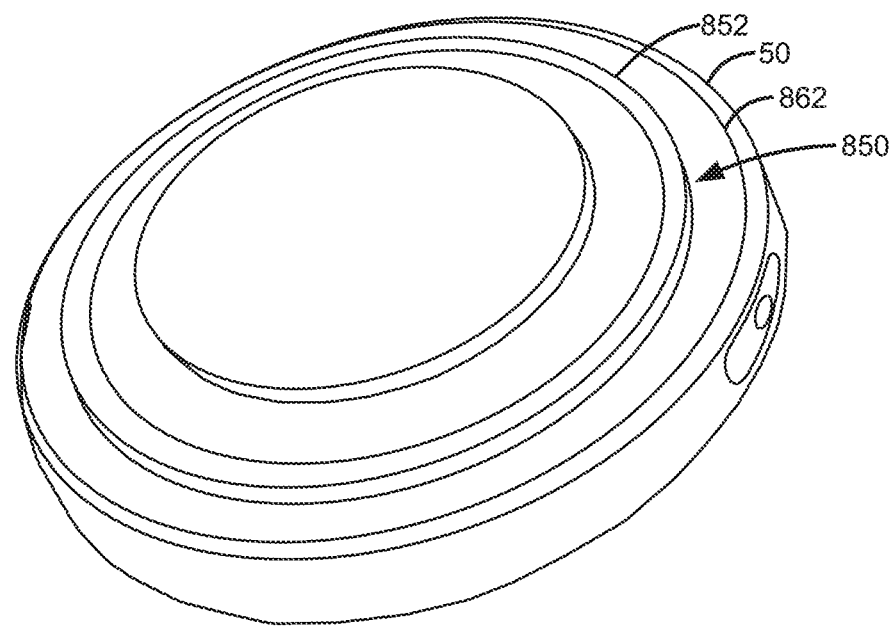

FIG. 12 is a schematic depiction of charging 900 of an IPG 10 via the CD 50. In some embodiments, charging can be performed by positioning the CD 50 in proximity and/or adjacent to the IPG 10. In some embodiments, this positioning of the CD 50 can include communication between the CD 50 and the IPG 10 to determine an optimal position of the CD 50 with respect to the IPG 10. In some embodiments, the use of a coil of a first type, such as a planar winding 852, in the CD 50 and a coil of a second type, such as an elongate winding 800, in the IPG 10 can simplify the positioning of the CD 50 with respect to the IPG 10.

In some embodiments, for example in which the IPG 10 is implanted such that at least one of axes 802, 809 is parallel and/or substantially parallel with the skin surface closest to the IPG 10 and/or from which charging of the IPG 10 is intended, the use of a planar winding 852 in the CD 50 combined with an elongate winding 800 in the IPG 10 can eliminate the need to control the rotational orientation of the CD 50 with respect to the IPG 10. This can simplify the positioning of the CD 50 with respect to the IPG 10. Specifically, the effect of the relative rotational orientation of the CD 50 with respect to the IPG 10 is diminished when the IPG 10 and the CD 50 have a relative orientation such that the axes 802, 809 of the charging circuit 15 of the IPG 10 are nonparallel to the winding axis 854 and/or the core axis 864, and/or have a relative orientation such that the axes 802, 809 of the charging circuit 15 of the IPG 10 are perpendicular and/or substantially perpendicular to the winding axis 854 and/or the core axis 864. In such an embodiment, effective energy transfer between from the CD 50 to the IPG 10 can be achieved by positioning the CD 50 proximate to the IPG 10 without having to also controlling the rotational orientation of the CD 50 about the CD axis 55. As rotational orientation of the CD 50 does not need to be controlled, the positioning of the CD 50 for recharging of the IPG 10, and thus recharging of the IPG 10 is simplified.

As a part of positioning, or subsequent to positioning of the CD 50 with respect to the IPG 10, the CD 50 can power the sending coil assembly 850, and specifically, the charging module 704 can power the sending coil assembly 850. In some embodiments, this powering of the sending coil assembly 850 can comprise the generation of series of pulses by the driver 708, the pulses timed to cause resonance in the charging circuit 706. These pulses can be delivered to the charging circuit 706 and can generate resonance in the charging circuit 706 at the resonant frequency of the charging circuit 706 and/or at another desired frequency. Through this powering of the charging circuit 706, and the current oscillations at the charging circuit 706, a magnetic field can be generated by the sending coil assembly 850. The magnetic field can be directed away from the circuitry 870 of the CD 50 by the core 862 of the sending coil assembly 850. The magnetic field can be generated until the CD 50 determines to terminate charging of the IPG 10 and/or until the CD 50 is instructed to terminate charging of the IPG 10.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A neurostimulation system for delivering one or more electrical pulses to a target region within a patient's body, the system comprising:
    an implantable neurostimulator for delivering the one or more electrical pulses, the implantable neurostimulator comprising:
    a hermetic housing comprising a biocompatible material;
    an energy storage feature configured to power the implantable neurostimulator;
    a receiving coil assembly comprising an elongate wire winding wound around a first ferritic core; and
    control circuitry configured to control recharging of the energy storage feature; and
    a charging device for wirelessly delivering energy to the implantable neurostimulator, the charging device comprising:
    a sending coil assembly comprising a planar wire winding on a surface of a second ferritic core, wherein the planar wire winding and the second ferritic core are non-coaxial such that an axis of the core that extends through the centerline of the second ferritic core is non-coaxial with a winding axis of the planar wire winding.

2. The neurostimulation system of claim 1, wherein the elongate wire winding extends parallel to a central axis of the first ferritic core, and wherein a winding axis of the planar wire winding is parallel to the core axis of the second ferritic core.

3. The neurostimulation system of claim 1, wherein the winding axis extends along a centerline of the planar wire winding, and wherein the core axis of the second ferritic core is perpendicular to the surface of the second ferritic core.

4. The neurostimulation system of claim 3, wherein the winding axis of the planar wire winding is laterally offset with respect to the core axis of the second ferritic core.

5. The neurostimulation system of claim 4, wherein the winding axis and the core axis are parallel.

6. The neurostimulation system of claim 1, the charging device further comprising charging circuitry for controlling powering of the sending coil assembly to generate a magnetic field to transfer power to the implantable neurostimulator.

7. The neurostimulation system of claim 6, wherein the second ferritic core is positioned between the planar wire winding and the charging circuitry.

8. The neurostimulation system of claim 7, wherein the second ferritic core is configured to isolate the charging circuitry from the magnetic field.

9. The neurostimulation system of claim 7, wherein the charging circuitry is isolated from the magnetic field via the second ferritic core.

10. The neurostimulation system of claim 1, wherein the second ferritic core comprises a disk.

11. The neurostimulation system of claim 10, wherein the first ferritic core comprises a rod.

12. A method of charging an implantable neurostimulator with a charging device, the method comprising:
    positioning a charging device adjacent to an implantable neurostimulator, the implantable neurostimulator comprising a receiving coil assembly; and
    generating a magnetic field via powering of a sending coil assembly of the charging device, the sending coil assembly comprising a planar wire winding on a surface of a second ferritic core and on top of the second ferritic core, wherein the second ferritic core is monolithic and wherein the planar wire winding and the second ferritic core are geometrically non-coaxial, such that an axis of the core that extends through the centerline of the second ferritic core is non-coaxial with a winding axis of the planar wire winding and wherein charging circuitry of the charging device is isolated from the magnetic field by the second ferritic core.

13. The method of claim 12, wherein the second ferritic core is positioned between the planar wire winding and the charging circuitry.

14. The method of claim 13, wherein the planar wire winding is off-center on the surface of the second ferritic core.

15. The method of claim 12, the receiving coil assembly comprising an elongate wire winding wound around a first ferritic core.

16. The method of claim 15, wherein the elongate wire winding extends parallel to a central axis of the first ferritic core, and wherein a winding axis of the planar wire winding is parallel to a core axis of the second ferritic core.

17. The method of claim 16, wherein when the charging device is positioned adjacent to the implantable neurostimulator, the central axis of the first ferritic core is non-parallel to the winding axis of the planar wire winding.

18. The method of claim 16, wherein when the charging device is positioned adjacent to the implantable neurostimulator, the central axis of the first ferritic core is perpendicular to the winding axis of the planar wire winding.

19. A neurostimulation system for delivering one or more electrical pulses to a target region within a patient's body, the system comprising:
    an implantable neurostimulator comprising:
    an energy storage feature configured to power the implantable neurostimulator; and
    an elongate receiving coil assembly; and a charging device for wirelessly delivering energy to the implantable neurostimulator, the charging device comprising:
a sending coil assembly comprising a planar wire winding coupled to and on a surface of a second ferritic core, wherein the second ferritic core has a center of mass located along a core axis along a centerline of the second ferritic core, and wherein a winding axis of the planar wire is non-coaxial with the core axis of the second ferritic core.

20. The neurostimulation system of claim 19, wherein the planar wire winding is centered on the surface of the second ferritic core.

21. The neurostimulation system of claim 19, wherein the charging device comprises charging circuitry for controlling powering of the sending coil assembly to generate a magnetic field to transfer power to the implantable neurostimulator, and wherein the ferritic core is positioned between the charging circuitry and the planar wire winding.

22. The neurostimulation system of claim 21, wherein the ferritic core is configured to isolate the charging circuitry from the magnetic field.

23. The neurostimulation system of claim 19, wherein the ferritic core comprises a disk.

24. The neurostimulation system of claim 19, wherein the elongate receiving coil assembly comprises an elongate wire winding wound around an elongate ferritic core.

* * * * *